United States Patent [19]
Jones et al.

[11] Patent Number: 5,677,432
[45] Date of Patent: Oct. 14, 1997

[54] IMMUNOLOGICAL DETECTION OF ORGANOPHOSPHATES

[75] Inventors: William Thomas Jones, Palmerston North, New Zealand; Hans Wynberg, Haren; Wolter Ten Hoeve, Eelde, both of Netherlands

[73] Assignee: The Horticulture and Food Research Institute of New Zealand Limited, Palmerston North, New Zealand

[21] Appl. No.: 290,841

[22] PCT Filed: Feb. 26, 1993

[86] PCT No.: PCT/NZ93/00010

§ 371 Date: Aug. 19, 1994

§ 102(e) Date: Aug. 19, 1994

[87] PCT Pub. No.: WO93/17030

PCT Pub. Date: Sep. 2, 1993

[30] Foreign Application Priority Data

Feb. 27, 1992 [NZ] New Zealand .............. 241759
Nov. 26, 1992 [NZ] New Zealand .............. 245281

[51] Int. Cl.$^6$ .............. C07K 16/44; C07K 17/00; C07F 9/6574
[52] U.S. Cl. .............. 530/404; 435/7.93; 435/345; 436/518; 436/815; 530/388.9; 530/389.8; 530/391.1; 530/391.3; 530/405; 530/406; 530/807; 544/214; 546/22; 546/25; 549/375; 558/84; 558/85; 558/86; 560/186
[58] Field of Search .............. 530/807, 404, 530/405, 406, 389.8, 391.1, 388.9, 391.3; 546/22, 25; 558/84, 86, 85; 544/214; 549/375; 560/186; 435/345, 7.93; 436/815, 518

[56] References Cited

FOREIGN PATENT DOCUMENTS 0003392 2/1968 Japan.
WO 91/00294 1/1991 WIPO.

OTHER PUBLICATIONS

J.H. Billman et al. "1,3,2–Dioxaphosphorinane 2–oxides . . . " Journal of Pharmaceutical Sciences, vol. 59 No. 6, Jun. 1970, pp. 861–863.

Dzantiev, B.B. et al. "Malathion antigen synthesis . . . " WPIL/Derwent SU1670608. Abstract.

Primary Examiner—Mary E. Ceperley
Attorney, Agent, or Firm—Nixon & Vanderhye

[57] ABSTRACT

A compound useful for forming immunoconjugates used in the detection of organophosphate pesticides is provided. The compound has the formula

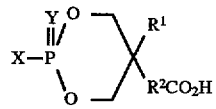

wherein X is selected from the group consisting of R—O—, R—S— and R—NH—, where R is an optionally substituted aromatic or heterocyclic group, or an optionally substituted alkyl or alkenyl group;

Y is O or S;

$R^1$ is H or alkyl; and $R^2$ is a group of the formula —$(CH_2)_n$— wherein n is an integer of from 1 to 10, or branched chain alkylene, or a group of the formula $R^3$—O—$R^4$ wherein $R^3$ and $R^4$ are both or straight or branched chain alkylene;

or a salt or ester thereof.

30 Claims, No Drawings

IMMUNOLOGICAL DETECTION OF ORGANOPHOSPHATES

TECHNICAL FIELD

The present invention relates to novel organophosphate compounds suitable for use as haptens, processes and novel intermediates for preparing the same, antibodies which are capable of binding to specific organophosphates, methods for preparing such antibodies, immunological assays employing such antibodies and assay kits including the antibodies.

BACKGROUND ART

Organophosphate pesticides are a large class of compounds commonly used as insecticides in the production of agricultural and horticultural produce. Legal maximum residue limits are stipulated by both national and international regulatory agencies for many of these compounds in most food crops and products. Increasingly, these levels are being monitored by the international and domestic agencies.

Accordingly, there is a need for internationally acceptable, simple, rapid, reliable, portable, sensitive and cost-effective assay systems for determining the presence of these organophosphate compounds. Immunoassay-based tests fulfil all these requirements. Modern immunoassays are based on two important phenomena: (i) the extraordinary discriminatory power of antibodies; (ii) detection systems that allow the reaction of the antibody with its hapten to be quantitated at low concentrations of the reactants (antibody and hapten). A plethora of labels has been applied as detecting agents in immunoassays such as enzymes, radioactive tracers, chemiluminescent and fluorescent labels, metal atom and sols, stable free radicals, latexes and bacteriophage.

The use of enzymes, enzyme immunoassays (EIA) and solid phase technology has brought about widespread use of these techniques. An excellent review of enzyme immunoassay is provided by Tijssen P, "Practice and theory of enzyme immunoassays" in Laboratory techniques in biochemistry and molecular biology, Elsevier Amsterdam, New York, Oxford ISBN 0-7204-4200-1 (1990).

Antibodies have proven useful reagents for the detection, quantitation and purification of large antigenic molecules and small biological and synthetic organic molecules. The former group can be injected into animals without further modification, and providing a suitable immune response is evoked will result in antibodies that recognise the antigen.

Small molecules ($M_R<1,000$) are usually unable to invoke an immune response when injected into animals. These molecules therefore have to be conjugated to larger immunogenic molecules (carriers). The small molecules then behave as an array of epitopes which in the presence of T cell receptors on the carrier can give rise to an immune response resulting in the production of antibodies by the differentiated B-lymphocytes.

Small molecules frequently need to be modified by introducing a spacer arm together with a functional group that can be utilised to conjugate the small molecule to the carrier. Placement of the linker/functional group on the small molecule will define the epitope that the antibodies recognise. If a choice exists, and one wishes to produce antibodies specific for the molecule, one should place the linker in such a position that it is spatially distant from any unique structural features on the molecule. Another consideration regarding the linker relates to size and possible antigenicity of the linker arm itself since these can act as immunogens themselves and give rise to unwanted antibodies. Another problem frequently encountered is that the molecule and linker arm may form a new unit, and stimulate the immune system to produce antibodies that recognise the new unit but may not recognise or have only a low affinity for the desired molecule. In such cases the antibodies are of no practical use.

All of these problems need to be addressed when considering the production of antibodies to small molecules.

The organophosphate group of pesticides, being small molecules, are not immunogenic nor can the majority of them be readily conjugated to a suitable carrier protein when in their usual chemical state to render them antigenic. A particular drawback in the production of reagent antibodies necessary for the development of immunoassay-based test methods has been the requirement to synthesise new molecules that are structurally similar to the organophosphate pesticide but also containing a functional group that can be used to conjugate the molecule to a suitable antigenic protein. This has been a major hurdle to international research and has hindered considerably efforts aimed at developing immunoassay-based methods for detecting many of the toxic or hazardous organophosphates.

One attempt to resolve this problem is described in PCT patent specification WO 91/00294. This specification discloses the chemical activation of organophosphorus pesticides (fenitrothion and closely related organophosphates) by means of derivatisation through a phosphorus atom by means of a protected ester or acid of a spacer-arm compound, beta-alanine.

This method is only relevant, however, to organophosphates of the general class

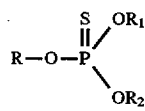

where R is an optionally substituted aromatic or heterocyclic group and $R_1$ and $R_2$ are each independently methyl or ethyl and not to the other major organophosphate classes. It therefore has the major disadvantage that it is not applicable to the production of antibodies to all organophosphates.

SUMMARY OF THE INVENTION

It is an object of the present invention to go some way towards overcoming the disadvantages of the prior art, or at least to offer the public a useful choice.

In a first aspect, the present invention may broadly be said to consist in a compound of the formula

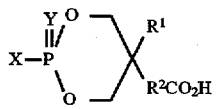

(I)

or a salt or ester thereof,
wherein X is selected from the group consisting of R—O, R—S or R—NH,
where R is an optionally substituted aromatic or heterocyclic group, or an optionally substituted alkyl or alkenyl group;
Y is selected from O or S;
$R^1$ is H or alkyl; and
$R^2$ is a group of the formula —$(CH_2)_n$ wherein n is an integer from 0 to 10 (preferably 0 to 6), or branched chain alkylene, or a group of formula R³—O—R⁴ wherein R³ and R⁴ are both straight or branched chain alkylene.

In further aspects the invention consists in compounds of the formulae:

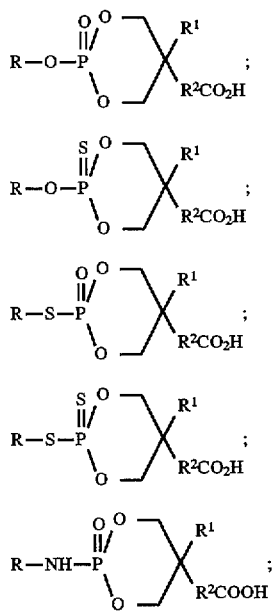

and

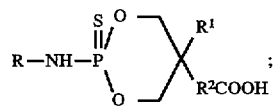

wherein R, R¹ and R² are as defined above.

In still a further aspect, the present invention consists in a compound of the formula

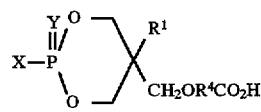

or a salt or ester thereof,
wherein
X and Y are as defined above;
R¹ is —H, —CH₃, or —CH₂CH₃; and
R⁴ is as defined above.

In another aspect, the invention consists in an antibody or binding fragment thereof capable of binding to both a compound of formula (I) as defined above and an organophosphate compound of the formula

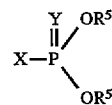

wherein X is selected from the group consisting of R—O, R—S and R—NH where R is an optionally substituted aromatic or heterocyclic group or an optionally substituted alkyl or alkenyl group; Y is O or S; and R⁵ is alkyl.

Conveniently, the antibody is a monoclonal antibody.
Alternatively, the antibody is a polyclonal antibody.

In yet a further aspect, the invention consists in an immunoconjugate comprising a compound of formula (I) or formula (IV) conjugated to an antigenic macromolecule.

In a further aspect, the invention consists in a method for producing an antibody or fragment thereof comprising the step of immunising an animal with an immunoconjugate as defined above.

The invention further provides antibodies or antibody fragments produced by the method as defined above.

In an additional aspect, the invention provides a method of producing a hybridoma cell line which comprises the step of immortalising an antibody-producing cell obtained from an animal immunised with an immunoconjugate as defined above.

The invention also provides hybridoma cell lines which are produced by such a method, as well as monoclonal antibodies secreted by such cell lines.

In particular, the invention provides monoclonal antibodies capable of specifically binding to an organophosphate compound of the formula:

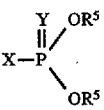

wherein X is selected from the group consisting of R—O, R—S and R—NH where R is an optionally substituted aromatic or heterocyclic group or an optionally substituted alkyl or alkenyl group, Y is O or S, and R⁵ is alkyl.

In an additional aspect, the invention provides a method for producing an antibody or binding fragment comprising the step of expressing DNA coding therefor in a recombinant host cell, said DNA having been obtained from an antibody-producing cell of an animal immunised with an immunoconjugate as defined above, wherein said antibody-producing cell is a spleen cell.

The invention further provides antibodies or binding fragments which are produced by such a method, and in particular recombinant antibodies or binding fragments which are capable of specifically binding to an organophosphate compound of the formula:

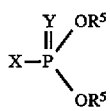

In still a further aspect, the invention consists in a method for detecting the presence of an organophosphate in a sample which may contain the organophosphate, said method comprising the step of assaying said sample with an antibody or fragment thereof as defined above.

In a further aspect, the invention provides an assay kit for detecting the presence of an organophosphate in a sample which may contain said organophosphate, said kit including an antibody to said organophosphate or a binding fragment of the antibody as defined above.

Conveniently, the kit will include an immunoconjugate as defined above.

In yet a further aspect, the invention provides a method of isolating an organophosphate compound from a sample which comprises the steps of:

(a) contacting said sample with an antibody or fragment thereof as defined above; and (b) recovering any organophosphate compound bound by said antibody or fragment.

In still a further aspect, the invention provides a method of cleansing an environmental medium contaminated with an organophosphate compound which comprises the step of contacting said medium with an antibody or fragment as defined above to remove said compound from said medium.

In further aspects, the invention provides processes for the preparation of compounds of formula (I) as will be described herein, together with various novel intermediate compounds formed during such preparative processes.

DETAILED DESCRIPTION OF THE INVENTION

While the present invention is broadly as defined above, it will be appreciated by those persons skilled in the art that it is not limited thereto but that it also includes embodiments of which the following description provides examples. In particular, the various aspects of the invention will be better understood with reference to the more detailed description provided below.

A. ORGANOPHOSPHATE HAPTENS

In its primary aspect, the invention provides novel organophosphate compounds (herein called "haptens").

These haptens are broadly based upon organophosphate compounds having the formula:

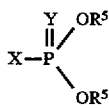

wherein X is R—O, R—S or R—NH, with R being an optionally substituted aromatic or heterocyclic group or an optionally substituted alkyl or alkenyl group, Y is O or S and $R^5$ is alkyl.

The haptens of the invention are required to be suitable for conjugation to an appropriate macromolecule (such as a protein) to form an immunoconjugate to which antibodies can be raised. To meet this requirement, the haptens of the invention have the general formula (I) as defined above. In formula (I), X can be R-O, R-S or R-NH; and Y can be O or S; with the different values for X and Y providing compounds of formulae (IA), (IB), (IC), (ID), (IE) and (IF) respectively.

In the above formulae, R can have any value which defines the specific "parent" organophosphate. R is therefore any optionally substituted aromatic heterocyclic group or an optionally substituted alkyl or alkenyl group. Some typical values for R are set out in Table 1.

TABLE 1

| Organophosphate | R |
|---|---|
| | R—O—P(=O) |
| Crotoxyphos | CH₃\C=C/H, COOCHCH₃(C₆H₅) |
| Dichlorvos | —CH=CCl₂ |
| Dicrotophos | —C(CH₃)=CH—CON(CH₃)₂ |

TABLE 1-continued

| Organophosphate | R |
|---|---|
| Mevinphos | —C(CH₃)=CHCOOCH₃ |
| Naled | —C(H)(Br)—C(Br)(Cl)—Cl |
| Paraoxon | —C₆H₄—NO₂ |
| | R—O—P(=S) |
| Chlorpyrifos | 3,5,6-trichloropyridin-2-yl |
| Coumithoate | (coumarin derivative) |
| Demeton | —(CH₂)₂SC₂H₅ |
| Diazinon | 2-isopropyl-6-methylpyrimidin-4-yl |
| Fenitrothion | 3-methyl-4-nitrophenyl |
| Fenthion | 3-methyl-4-methylthiophenyl |
| Isofenphos | 2-(COOCH(CH₃)₂)phenyl |
| Parathion | —C₆H₄—NO₂ |
| Propetamphos | CH₃\C=C/H, COOCH(CH₃)₂ |

TABLE 1-continued

| Organophosphate | R |
|---|---|
| Ronnel | (2,4,5-trichlorophenyl group) Cl, Cl, Cl |
| Thionazin | (pyrazinyl group with two N) |
| Pyrimiphos-ethyl | (pyrimidinyl group with N(CH$_2$CH$_3$)$_2$, N, CH$_3$ substituents) |

$$R-S-\overset{O}{\underset{\parallel}{P}}$$

| Demeton | —(CH$_2$)$_2$SC$_2$H$_5$ |
| Echothiophate | —CH$_2$CH$_2$N$^+$(CH$_3$)$_3$I$^-$ |

$$R-S-\overset{S}{\underset{\parallel}{P}}$$

| Azinphos methyl | (benzotriazinone-CH$_2$— group) |
| Dimethoate | —CH$_2$CONHCH$_3$ |
| Disulfoton | —CH$_2$CH$_2$SC$_2$H$_5$ |
| Malathion | —CH.COOC$_2$H$_5$ <br> \| <br> CH$_2$COOC$_2$H$_5$ |
| Methidathion | (structure with O, S, OCH$_3$, —CH$_2$—N—N) |
| Phosmet | (phthalimido-CH$_2$— group) |
| Phorate | —CH$_2$.S.C$_2$H$_5$ |
| Terbufos | —CH$_2$SC(CH$_3$)$_3$ |
| Dialifor | (phthalimido group with CH$_2$Cl, —CH—N substituent) |

TABLE 1-continued

| Organophosphate | R |
|---|---|
| Carbophenothion | 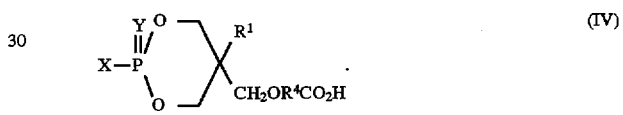 |

In the above formulae, $R^1$ can be hydrogen, or any alkyl group (particularly $C_1$–$C_6$ alkyl). However, where as is preferred, the hapten is to be conjugated to a protein macromolecule and used in the production of antibodies, $R^1$ will usually be selected from hydrogen, —CH$_3$, or —CH$_2$CH$_3$ with $R^1$ being H or —CH$_3$ being presently most preferred.

In the above formulae, $R^2$ is selected from a group of the formula —(CH$_2$)$_n$— wherein n is an integer from 0 to 10, more preferably an integer from 0 to 6, or branched chain alkylene or a group of the formula $R^3$—O—$R^4$ wherein $R^3$ and $R^4$ are independently straight or branched chain alkylene.

In a preferred embodiment, $R^2$ is a group of the formula $R^3$—O—$R^4$ wherein $R^3$ is —CH$_2$— and $R^4$ is a straight or branched chain alkylene. This embodiment provides a subclass of compounds of formula (I) having the formula (IV)

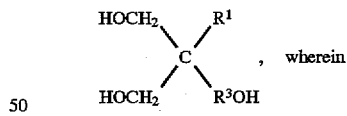

(IV)

A most preferred embodiment of the invention is a compound of formula (IV) in which X and Y are as defined above, $R^1$ is hydrogen or —CH$_3$ and $R^4$ is —CH$_2$—.

B. PREPARATION OF ORGANOPHOSPHATE HAPTENS

Compounds of formulae IA, IB and ID, wherein $R^2$ is $R^3$—O—$R^4$ may be prepared using the reaction scheme shown as Synthetic Route A and described generally below in B1(i), B2 and B4.

This reaction scheme is based on the use of a triol of the general formula $$\begin{array}{c} HOCH_2 \\ \phantom{HOCH_2}\diagdown \phantom{R^1} \diagup R^1 \\ \phantom{HOCH_2 HH} C \\ \phantom{HOCH_2}\diagup \phantom{R^1} \diagdown R^3OH \\ HOCH_2 \end{array} \text{, wherein}$$

$R^1$ is H or alkyl and $R^3$ is alkyl. The triol 2-hydroxymethyl-2-methyl-1,3-propanediol is readily commercially available at low cost and provides a convenient starting material.

An alternative general method of preparing compounds of formula IA in which $R^2$ is $R^3$—O—$R^4$ is described in B.1(ii).

Compounds of formula IC wherein $R^2$ is $R^3$—O—$R^4$ may be prepared as described generally in B.3 below.

Compounds of formula I wherein $R^2$ is —(CH$_2$)$_n$— or branched chain alkylene may be prepared using reaction schemes shown as Synthetic Routes B and C and described in B.6 below.

Compounds of formula IE and IF wherein $R^2$ is $R^3$—O—$R^4$ may be prepared as described generally in B.5 below.

Synthetic Route A
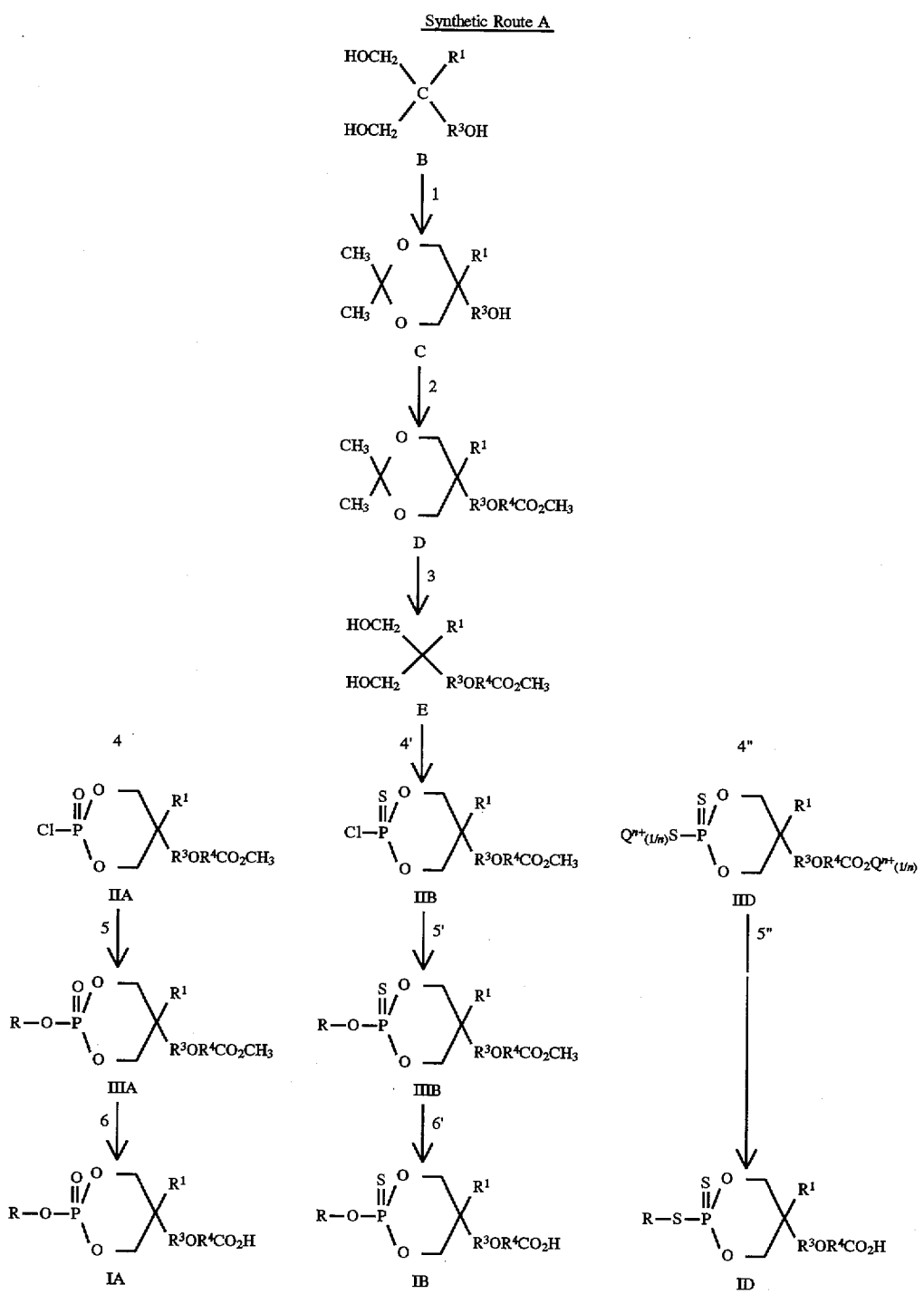
Synthetic Route B
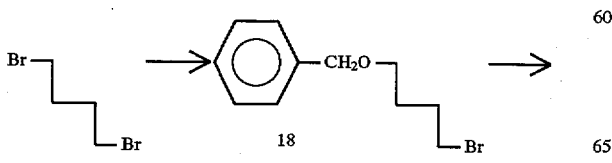
-continued
Synthetic Route B
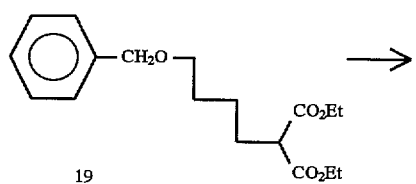

-continued
Synthetic Route B

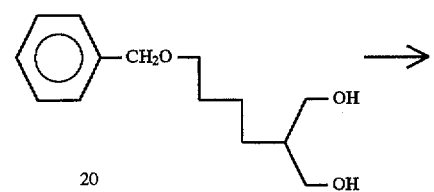

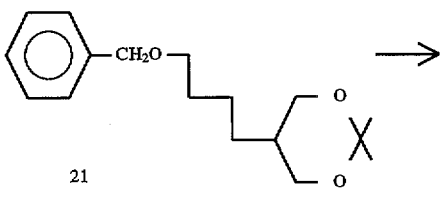

-continued
Synthetic Route B

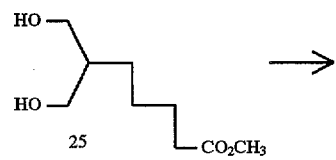

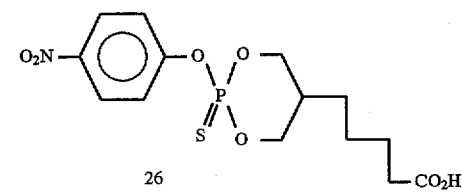

Synthetic Route C

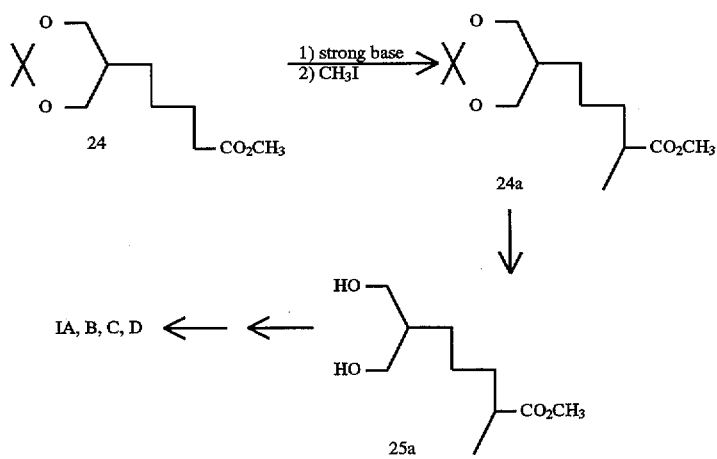

-continued
Synthetic Route B

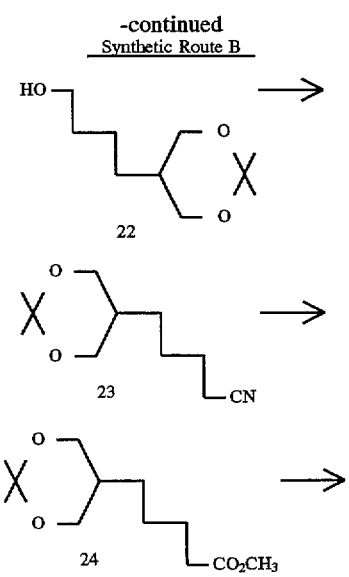

It will be appreciated that most if not all of the intermediate compounds outlined in Synthetic Routes A, B and C are novel. Such intermediate compounds provide yet a further aspect to this invention.

B.1(i) Preparation of Compounds of Formula IA according to Synthetic Route A (e.g. hapten to paraoxon)

1. A compound of formula IA may be prepared, starting with a known alcohol of formula B and protecting it as the acetone ketal in a known manner to give a compound of formula C (*J Org.Chem* 37 2197 (1972)).

2. The compound C is (1) alkylated using, for example, a halo-substituted carboxylic acid, and (2) esterified to obtain a compound of formula D.

3. The acetal moiety is deprotected under mild conditions (e.g. using pyridinium p-toluene sulfonate) to give a diol of formula E.

4. The diol E may be converted to a cyclic acid chloride (as a mixture of isomers) of formula IIA by reaction with phosphoryl chloride.

5. Conversion to the haptens of formula IIIA (as esters, and again as a mixture of isomers) may be achieved by reaction with the anion of the desired alcohol (typically an aromatic alcohol) in a suitable solvent such as di-methyl formamide (DMF).

6. To obtain the hapten of formula IA, the carboxylic moiety is selectively hydrolysed (without hydrolysing the phosphate ester). A preferred reagent for achieving the selective hydrolysis is potassium carbonate.

B.1(ii) Alternative Method of Preparation of Compounds of Formula IA (e.g. hapten to dichlorvos)

Alternatively, a compound of formula IA may be prepared by reacting a compound of the formula E (shown in Synthetic Route A) with trimethylphosphite and triethyl amine, to yield a compound of the formula

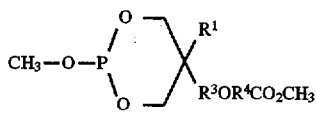
(VI)

The compound of formula VI so obtained may be reacted with a compound of formula

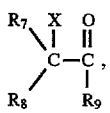

wherein X is a halogen (for example chloral) to yield a methyl ester of formula VII:

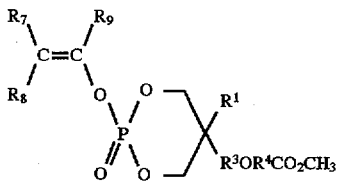
(VII)

The methyl ester may then be selectively hydrolysed to yield a combed of formula (VIII) (a sub-class of compounds of the formula IA)

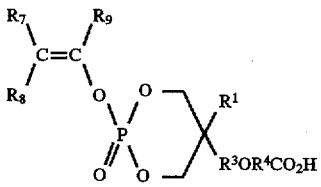
(VIII)

$R^7$, $R^8$ and $R^9$ can have any value which defines the specific "parent" organophospate. $R^7$, $R^8$ and $R^9$ are therefore each independently hydrogen or any optionally substituted aromatic or heteroyclic group or an optionally substituted alkyl or alkenyl group.

B.2 Preparation of Compounds of Formula IB according to Synthetic Route A (e.g. hapten to chlorpyrifos or parathion)

The steps 1 to 6 outlined above in paragraph B.1(i) for a compound of formula IA are followed with the variation that thiophosphoryl chloride (instead of phosphoryl chloride) is reacted with the diol E to give a compound of formula IIB (step 4') which may then be converted to the hapten ester of Formula IIIB in a similar manner, i.e. by reaction with the anion of the desired alcohol ROH (step 5'). The carboxylic ester so obtained is selectively hydrolysed using, for example, either lithium hydroxide or, more preferably, potassium carbonate, to give a compound of formula IB.

Preferred compounds of formula IB are those in which R is an optionally substituted aromatic, heterocyclic or alkenyl group. When R is an alkyl group, the compound of formula IB is less stable and may partially rearrange to a compound of formula IC.

B.3 Preparation of Compounds of Formula IC (e.g. hapten to demeton)

1. An alcohol of the formula $R^{10}$—OH wherein $R^{10}$ is an optionally substituted alkyl group (for example ethylthioethanol with nBu-Li) is reacted with a compound of the formula IIB (which maybe be prepared as described in paragraph B.2 herein), to yield a compound of formula (IX)

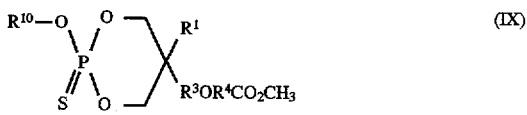
(IX)

2. The compound of formula (IX) so obtained is selectively hydrolysed (for example using $K_2CO_3$) and acidified (for example using Hcl).

3. The product of step 2 will slowly isomerise to yield the more stable thiophosphoric O,O,S-tri-ester of the formula IC defined above, wherein $R^2$ is $R^3$—O—$R^4$. To effect the isomerisation, the product of step 2 may for example, bestirred in toluene at room temperature for some days.

B.4 Preparation of Compounds of Formula ID according to Synthetic Route A (e.g. hapten to azinphos)

A compound of formula E, obtained using the sequence of steps described above, is reacted with phosphorus pentasulphide and a base to produce a salt of formula IID (step 4"). Preferably, potassium hydroxide in methanol is used to prepare the bispotassium salt, in which $Q^{n+}$ is $K^+$. The salt IID is then treated with a strong acid to protonate the carboxylate, followed by reaction with a compound of formula $R^6$—$CH_2Y$ (in which Y is a halogen and $R^6$ is defined as for R) to yield the desired hapten (step 5"). For example, to obtain a hapten for azinphos, the salt IID may be treated with one equivalent of hydrochloric acid, followed by reaction with chloromethylbenzotriazinione.

B.5 Preparation of Compounds of Formula IE and IF

The steps 1 to 4 or 4' of Synthetic Route A are first carried out, to prepare a compound of either formula IIA (if a compound of formula IE is desired) or formula IIB (if a compound of formula IF is desired).

The compound of formula IIA or IIB so obtained is then treated with the anion of an amine of the formula R—$NH_2$ (wherein R is as defined for formula IA), to yield a compound of the formula

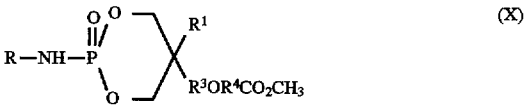
(X)

from a compound of formula IIA, or

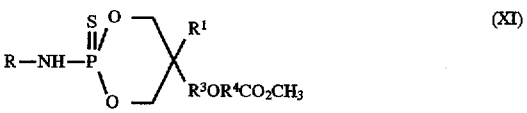
(XI)

from a compound of formula IIB.

The compound of formula (X) or (XI) is then selectively hydrolysed, for example using potassium carbonate, to yield a compound of formula IE or IF respectively.

B.6 Preparation of Compounds of Formula I in which $R^2$ is —$(CH_2)_n$— or branched chain alkylene A compound of the formula (I) wherein $R^1$ is H and $R^2$ is —$(CH_2)_n$ may be prepared using Synthetic Route B. The specific reaction scheme shown in Synthetic Route B is the preparation of a hapten to the organophosphate parathion. The reagents used in each step are detailed in the examples following which describe the preparation of the compound 26.

If it is desired to prepare haptens to organophosphate compounds other than parathion, the final steps of the synthetic procedure (from compound 25 on) may be substituted with the appropriate steps analogous to the final steps of Synthetic Route A (from compound E on), depending on the compound of formula (I) desired to be prepared.

It is also possible to prepare compounds of formula (I) in which $R^2$ is longer or shorter than the —(CH$_2$)$_4$— group shown in the reaction scheme, by using a longer or shorter dihaloalkane than 1,4 dibromobutane as a starting material.

Compounds in which $R^2$ is a branched chain alkylene may also be prepared, preferably by synthetic Route B, using a substituted dihaloalkane as a starting material, for example

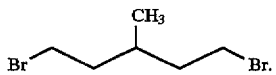

Alternatively, branched chain compounds may be prepared using Synthetic Route C. A compound of formula 24 (or an analogous compound having a longer or shorter $R^2$ group) is first prepared using Synthetic Route B. The compound of formula 24 thus prepared is then treated with strong base followed by CH$_3$I to obtain a compound of formula 24a. The final steps in the procedure are again analogous to those of Synthetic Route A.

If it is desired to prepare a compound of formula (I) in which $R^2$ is —(CH$_2$)$_n$— and $R^1$ is alkyl, Synthetic Route B may be modified accordingly. For example, a compound in which $R^1$ is —CH$_3$ and $R^2$ is —(CH$_2$)$_4$— may be prepared by reacting a compound of formula 19 (shown in Synthetic Route B) with a strong base and CH$_3$I to yield a compound of the formula

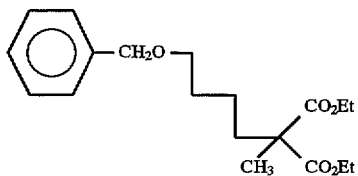

19a

The compound 19a may then be converted to a compound of formula I by carrying out the remaining steps of Synthetic Route B.

B.7 EXAMPLES

In the following examples, the compounds numbered 8 and 10 are compounds of formula (IB) wherein $R^1$ is —CH$_3$ and $R^2$ is —CH$_2$—O—CH$_2$—, and were prepared using Synthetic Route A. Compound 12 is a compound of formula (IA) wherein $R^1$ is —CH$_3$ and $R^2$ is —CH$_2$—O—CH$_2$—, and was also prepared using Synthetic Route A. Compounds 13 and 16 are compounds of formula (ID) wherein $R^1$ is —CH$_3$ and $R^2$ is —CH$_2$—O—CH$_2$—, and were prepared using Synthetic Route A.

Compound 15 is a compound of formula (IA) wherein $R^1$ is —CH$_3$ and $R^2$ is —CH$_2$—O—CH$_2$—, and was prepared using the reaction scheme described generally in B.1(ii) above. Compound 17 is a compound of formula (IC) wherein $R^1$ is —CH$_3$ and $R^2$ is —CH$_2$—O—CH$_2$, and was prepared using the reaction scheme described generally in B.3 above.

Compound 26 is a compound of the formula (ID) wherein $R^1$ is H and $R^2$ is —(CH$_2$)$_4$—, and was prepared using Synthetic Route B, described generally in B.6.

In the examples, the structural formulae of compounds 1 to 17 are illustrated. The structural formulae of compounds 18 to 26 are illustrated in Synthetic Route B above.

In all cases, the compound numbers referred to as starting materials in the preparative procedures described in the examples correspond to the specific compounds the preparation of which is described in preceding examples.

5-hydroxymethyl-2,2,5-trimethyl-1,3-dioxane 1 (see Gash, V W, *J Org Chem* 37 2197 (1972))

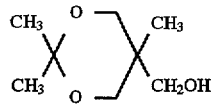

A mixture of 2-hydroxymethyl-2-methyl-1,3-propanediol (240 g, 2 mol), acetone (120 g, 2 mol), a few crystals of p-toluenesulfonic acid, and 800 ml benzene is heated under reflux for 24 h with azeotropic removal of water. The reaction mixture is concentrated by rotary evaporation, and the residue is purified by bulb-to-bulb distillation. This affords 288.8 g (1.805 mol, 90%) of the desired alcohol with bp 80° C./0.2 mmHg.

2-(2,2,5-trimethyl-1,3-dioxan-5-yl)methoxyacetic acid, methyl ester 2

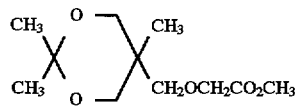

To 188 g sodium hydride dispersion (50–55% in mineral oil, washed once with hexane; 2.46 mol) there is added 2000 ml toluene, followed by 178 g (1.11 mol) of the alcohol 1, dissolved in about 100 ml toluene. This mixture is stirred and heated under nitrogen for 1.5 h at 60°–70° C. The greyish suspension is cooled, and 187 g (1.36 mol) bromoacetic acid, dissolved in 200 ml toluene (it is dissolved in toluene by first melting it), is added in 45 m with ice-cooling (foaming, the temperature of the reaction mixture is between 20 and 30° C.). The reaction mixture is warmed up, 500 ml toluene being added for efficient mixing, and then heated under reflux for 2 days with mechanical stirring. A suspension with much solid materials attached to the glasswall results after this period. The toluene is removed as well as possible by rotary evaporation and to the residue there is added 3000 ml DMF. The mixture is stirred for about 2 h, i.e. until the solids are fairly well suspended in DMF. The suspension is cooled with ice to about 10° C. (a lower temperature gives solidification) and iodomethane (200 g, 1.408 mol) in 200 ml DMF is added with stirring and cooling.

After stirring for 3 d at RT the well-stirrable suspension is rotary evaporated. Toluene (2 l) and 10% sodium bicarbonate solution (1 l) are added to the residue with stirring. The mixture is then filtered under vacuum, the solids being washed with 500 ml water and 500 ml toluene. The organic layer is separated and washed with 1 l water, then dried over a mixture of sodium sulfate and some potassium carbonate, filtered and evaporated. Bulb-to-bulb distillation at 0.2 mmHg affords 175 g (0.754 mol, 68%) of the desired product. $^1$H-NMR (CDCl$_3$): δ 0.85 (s, 3H), 1.35 (s, 3H), 1.40 (s, 3H), 3.5–3.7 (AB, 4H), 3.5 (s, 2H), 3.7 (s, 3H), 4.1 (s, 2H). $^{13}$C-NMR (CDCl$_3$):δ17.9, 20.7, 26.6, 34.3, 51.6, 66.2, 68.7, 74.5, 97.8, 170.9.

Alternative Method of Preparation of 2-(2,2,5-trimethyl-1, 3-dioxan-5-yl)methoxyacetic acid, methyl ester 2

To 157 g sodium hydride dispersion (55–65% in mineral oil, 3.60–4.25 mol, washed twice with 300 mL hexane) there is added 800 mL DMF, followed by 285 g (1.78 mol) of the alcohol 1 in 200 mL DMF in about 1 h (cooling with ice-water bath so that the temperature of the reaction mixture remains at 20°-30° C.). The mixture is stirred for 3 h at RT, then 249 g bromoacetic acid (1.79 mol) in 500 mL DMF is added over a 2 h period with ice-cooling and mechanical stirring (temperature of the reaction mixture remains at 16°-22° C.). A solid mass resulted shortly after all the acid had been added, therefore 1 L DMF was added in order to obtain a stirrable mass. The suspension is stirred overnight at RT, giving a partially solidified mixture, then warmed up to 30° C., giving a stirrable suspension. After stirring for 2 h at 30° C. there is added 210 mL dimethyl sulfate (2.22 mol) in 2 h at 30°-35° C. (some cooling is necessary). The thin suspension is stirred at RT for 5 h, then partially rotary evaporated in order to remove most of the DMF. To the residue there is added 1 L water and 1 L toluene, the mixture is shaken and the layers are separated. The aqueous layer is extracted with 750 mL toluene and the combined toluene layers are washed with 2×1 L water. After drying and evaporation of the toluene layer the residue is purified by bulb-to-bulb distillation. This affords 240.2 g of the desired product (1.035 mol, 58%).

2-(3-hydroxy-2-hydroxymethyl-2-methyl)propoxyacetic acid, methyl ester 3

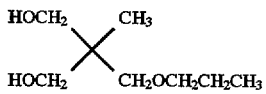

To a solution of the acetal ester 2 obtained above (96.0 g, 0.414 mol) in 450 ml methanol there is added 6.9 g pyridinium p-toluenesulfonate (27.5 mmol), followed by 120 ml water. The solution is stirred for 4 h. During this stirring period a total of 400 ml water is added in 100 ml portions. The resulting solution is rotary evaporated, 100 ml toluene is added to the residue, the solution is rotary evaporated, again 100 ml toluene is added and the solution is rotary evaporated. This leaves 90 g of residue which is used as such in subsequent reactions (attempted purification by bulb-to-bulb distillation led to lactonisation). $^1$H-NMR (CDCl$_3$):δ0.8 (s, 3H), 3.4 (s, 2H), 3.5 (s, 4H), 3.6 (s, 2H), 3.7 (s, 3H), 4.1 (s, 2H).

2-(2-chloro-5-methyl-1,3,2-dioxaphosphorinan-5-yl2-sulfide)methoxyacetic acid, methyl ester 4

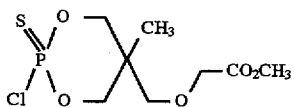

27.3 of the crude diol 3 obtained above (i.e. containing 3.1 g pyridinium p-toluenesulfonate) is dissolved in 100 ml toluene, then pyridine (25 ml, 0.316 mol) is added. The mixture is cooled to 10°-15° C., then thiophosphoryl chloride (distilled, 26 g, 0.153 mol) is added over a 3 m period (the temperature of the mixture rises to 25°-30° C.). The suspension is stirred overnight at RT, then poured in 250 ml water. Toluene (100 ml) is added, the mixture is shaken and the layers are separated. The organic layer is washed with 250 ml water, the aqueous layers are extracted with 100 ml toluene. The combined toluene layers are dried over sodium sulfate, then rotary evaporated. The residue is dissolved in some toluene and filtered over a column of aluminiumoxide (5×3 cm), the product being eluted with toluene. The filtrate is evaporated and the residue is stirred overnight with a mixture of 30 ml ether and 30 ml ligroin (bp 40°-60° C.).

After cooling to −10° C. for 2 h, the suspension is filtered with suction, the solid being washed with a 2/3 mixture of ether and ligroin. This gives 12.95 g of the product, which by NMR appears to be mainly 1 isomer. The filtrate of the crystallisation is evaporated, this leaves a residue of 12.72 g, which by NMR appears to be a 1/2 mixture of the crystalline and liquid isomer. Total yield 25.67 g (88.0 mmol, 71% yield based on acetal ester 2). The crystalline isomer has singlets at δ0.9, 3.7 and 4.1 ppm. Both isomers have multiplets in the δ3.8–4.8 ppm region.

2-(2-chloro-5-methyl-1,3,2-dioxaphosphorinan-5-yl,2-oxide)methoxyacetic acid, methyl ester 5

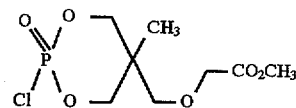

In a manner identical to the preparation of 4, the oxygen analogue 5 is prepared using phosphoryl chloride instead of thiophosphoryl chloride. After filtration of the crude product over aluminium oxide, and evaporation of the toluene eluate the product (21.8 g, 80 mmol, 63% yield based on the acetal ester 2) is obtained as an oily mixture of 2 isomers. Attempted purification through vacuum distillation resulted in almost complete decomposition. $^1$H-NMR(CDCl$_3$):δ1.0 (s), 1.3(s) (ratio about 2/1), 3.3–4.7 (m) with singlets at 3.4, 3.7 and 4.1.

2-(2-mercapto-5-methyl-1,3,2-dioxaphosphorinan-5-yl, 2-sulfide)methoxyacetic acid, bispotassium salt 6

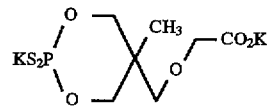

35.4 (0.184 mol) of the crude diol 3 obtained above is dissolved in 300 ml toluene. Phosphorus pentasulfide (35.4 g, 0.144 mol) is added and the suspension is stirred for 1 h at 60°–70° C., than at RT overnight, then at 80°–90° C. for 3 h (most of the phosphorus pentasulfide dissolves during the heating process). The mixture is filtered under vacuum, the solids being washed with some toluene. The filtrate is evaporated, 200 ml methanol is added to the residue, followed by the addition of 30 g potassium hydroxide in 100 ml methanol over a 15 m period (with cooling, the temperature rises to about 35° C.). The resulting suspension is filtered under vacuum, the solid being washed with methanol. This gives 31.9 g (91.7 mmol, 56% based on the acetal ester 2) of the colourless bispotassium salt 6. It can be recrystallised from a mixture of ethanol and water. $^1$H-NMR (D$_2$O): 1.0 (s, 3H), 3.5 (s, 2H), 3.9, 4.0, (s, 4H), 4.25 (s, 2H).

2-[5-methyl-2-(3,5,6-trichloropyridin-2-oxy)-1,3,2-dioxaphosphorinan-5-yl,2-sulfide]methoxyacetic acid methyl ester 7

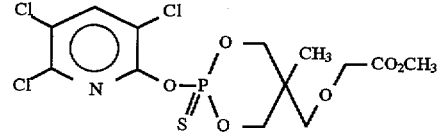

To sodium hydride in mineral oil (50–55%, 1.94 g, 44.4 mmol, washed twice with 40 ml ligroin) there is added 50 ml DMF, followed by trichloropyridinol (9.2 g, 46.3 mmol, added in portions over 10 m). After stirring for 30 m the crystalline isomer 4, obtained above, is added (10.15 g, 35.18 mmol), followed by 10 ml DMF. After stirring for 3 d at RT the mixture is poured on 500 ml water (containing 10 g sodium bicarbonate). The product is extracted with 500 and 250 ml chloroform, the combined organic layers are washed with 500 ml water, then dried and evaporated. The residue which solidifies on standing weighs 15.0 g. It can be purified by stirring with a 1/1 mixture of ether and ligroin, this gives the product as one isomer. $^1$H-NMR (CDCl$_3$:δ1.0 (s, 3H, 3.8 (s, 5H), 4.2 (s, 2H), 4.2–4.4 (m, 4H), 7.9 (s, 1H). $^{13}$C-NMR (CDCl$_3$:δ16.1, 36.2, 51.7, 68.5, 71.8, 73.9, 74.0, 121.0, 127.4, 141.1, 144.2, 150.2, 170.4. Similarly, from the oily mixture of chlorides 4 a mixture of esters 7 is obtained. The more soluble isomer has singlets at δ1.3, 3.3, 3.7, 3.9 and 7.9 ppm, and a multiplet at δ3.7–4.8 ppm.

2-[5-methyl-2-(3,5,6-trichloropyridin-2-oxy)-1,3,2-dioxaphosphorinan-5-yl,2-sulfide]methoxyacetic acid 8 (chlorpyrifos hapten)

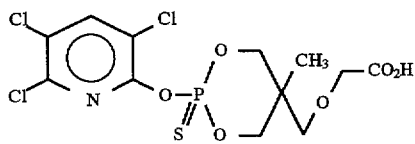

To the crude 7 (15.0 g) obtained above there is added 75 ml THF followed by 75 ml methanol. Over a period of 10 m a solution of potassium carbonate (5.28 g, 38.3 mmol) in 35 ml water is added, followed by the addition of 50 ml water over a 15 m period. After stirring for 2 h there is added 500 ml water. The mixture is extracted with 400 ml of a 3/1 mixture of toluene and ethanol and with 300 ml toluene. The combined organic layers are washed with 250 ml water, then dried and evaporated to give unreacted ester 7. The combined aqueous layers are acidified with 10 ml conc. Hydrochloric acid, then extracted with 4×250 ml toluene. The combined toluene layers are dried and rotary evaporated to give a residue which is dissolved in 100 ml warm methanol. Water (about 60 ml) is added, followed by some seed crystals. After stirring at RT for some time the precipitate is collected by vacuum filtration. It weighs 6.50 g which by NMR appears to be 1 isomer. From the filtrate there is obtained with the same procedure another 1.78 g of 8, which by NMR consists of a 3/2 mixture of the more soluble and less soluble isomer. Total yield 8.28 g (18.97 mmol, 54% yield based on chloride 4). Similarly, from the oily mixture of chlorides 4 obtained above the acid 8 is obtained (after the methanol-water purification) as a 5/2 mixture of the more soluble and less soluble isomer. $^1$H-NMR (CDCl$_3$) for the less soluble isomer: singlets at δ1.0 (3H), 3.7 (2H), 4.8 (2H), 7.8 (1H), and 8.9 (1H, broad) multiplet at δ3.8–4.9. The more soluble isomer has singlets at δ1.3, 3.4 (broad), and 7.8, and a multiplet at δ3.7–4.9.

2-[5-methyl-2-(4-nitrophenoxy)-1,3,2-dioxaphosphorinan-5-yl,2-sulfide]methoxyacetic acid, methyl ester 9

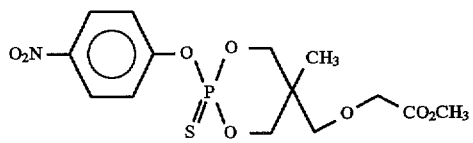

To a mixture of sodium hydride (1.10 g, 50–55%, 22.9 mmol, washed twice with 30 ml ligroin) and DMF (30 ml) there is added 3.00 g 4-nitrophenol (21.6 mmol) in 0.5 g portions. After stirring for 1 h 5.15 g (20 mmol) of crystalline chloride 4 is added and the mixture is stirred for 3 d at RT. The reaction mixture is poured in a 250 ml 4% sodium bicarbonate solution, the product is extracted with 250 ml toluene. Washing with 2×250 ml water, followed by drying and evaporation gives the crude product as a 3/2 mixture of isomers (by NMR). Addition of 50 ml ether gives a solid, after filtration and washing with ether it weighs 2.07 g (1 isomer by NMR, major isomer in the crude product). Similarly, from 5.15 g of the oily mixture of chlorides 4 a crude product is obtained, whose NMR is almost identical to the NMR of the crude product obtained from crystalline 4. Treatment with ether gives 1.59 g of 1 isomer. The ether filtrates of both products are combined, evaporated, treated with 50 ml ether and some ligroin, then stored at −15° C. to give 3.45 g of product 3/2 mixture of more soluble and less soluble isomer). Total yield: 7.31 g (18.7 mmol, 47% yield). $^1$H-NMR of less soluble isomer (CDCl$_3$: 1.0 (s, 3H), 3.7 (s, 5H), 4.1 (s, 4H), 4.35 (AB, 2H), 7.1–8.2 (AB, 4H). The more soluble isomer has a singlet at 1.3 ppm, and a complicated pattern in the 3.4–4.9 ppm range with singlets at 3.4, 3.7 and 4.0 ppm.

2-[5-methyl-2-(4-nitrophenoxy)-1,3,2-dioxaphosphorinan-5-yl,2-sulfide]methoxyacetic acid 10 (parathion hapten)

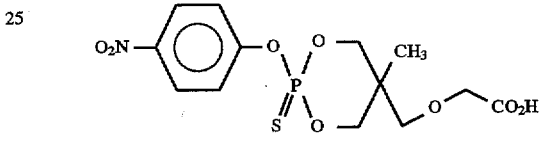

To 3.66 g (9.36 mmol) of less soluble ester 9 in 70 ml methanol there is added so much THF that a solution results (about 20 ml THF). Lithium hydroxide (232 mg, 9.65 mmol) in 20 ml 1/3 water/methanol is added with stirring in 30 m. The mixture is stirred for 1 h, then poured in 500 ml water. This solution is extracted with 250 ml toluene, which is washed with 50 ml water. The combined aqueous layers are acidified with 1.5 ml conc. hydrochloric acid, then extracted with 2×250 ml toluene. The toluene layers are dried and evaporated to give a solid residue, which is stirred with ether. Filtration and washing with ether gives 1.26 g of the less soluble isomer.

Similarly, from 3.45 g of the mixture of esters 9 obtained above, there is obtained 1.01 g of the more soluble isomer (isomer ratio 2/1) after treatment with ether. From the combined filtrates of both reactions another 0.79 g of an almost 1/1 mixture of isomers is obtained after treatment with ether. Total yield: 3.06 g (8.12 mmol, 43%). $^1$H-NMR of the less soluble isomer (CDCl$_3$δ:1.0 (s, 3H), 3.6–4.6 (m), 3.8(s), 4.2(s) (8H), 7.5–8.6 (AB, 4H). The more soluble isomer has singlets at δ1.3, 3.45 and 4.1 ppm.

2-[5-methyl-2-(4-nitrophenoxy)-1,3,2-dioxaphosphorinan-5-yl,2-oxide]methyoxyacetic acid, methyl ester 11

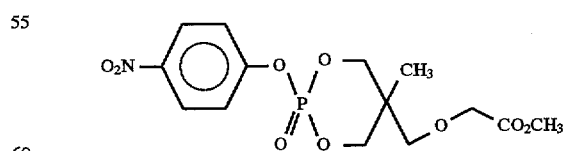

To a mixture of sodium hydride ((3.14 g, 50–55%, 72 mmol, washed twice with 40 ml ligroin) and 75 ml DMF thee is added over a 10 m period 10.2 g 4-nitrophenol (73.4 mmol). After stirring for an additional 30 m the chloride 5 (16.9 g, 62.0 mmol) in 20 ml DMF is added. The mixture is stirred for 3 d at RT, then poured in 500 ml 2% sodium bicarbonate solution. The product is extracted with 500 ml toluene, the toluene layer is washed with 2×500 ml water, then dried and evaporated. To the residue (consisting of 2 isomers in a 3/2 ratio) there is added 100 ml ether and the mixture is stirred for 2 h. The solid is filtered off and washed with ether to give 12.6 g of mainly the major isomer. Evaporation of the filtrate leaves 7.94 of mainly the other isomer. Total yield: 19.54 g (52.1 mmol, 84%). $^1$H-NMR of the less soluble isomer (CDCl$_3$):δ1.0 (s, 3H), 3.7 (s, 5H), 3.9–4.8 (m) and 4.15(s) (6H), 7.2–8.3 (AB, 4H). $^1$H-NMR of the more soluble isomer (CDCl$_3$:δ1.3H) 3.4 (s, 2H) 3.7 (s 3H) 3.9–4.9 (m) and 4.0(s) (6H), 7.2–8.3 (AB, 4H).

2-[5-methyl-2-(4-nitrophenoxy)-1,3,2-dioxaphosphorinan-5-yl,2-oxide]methoxyacetic acid 12 (paraoxon hapten)

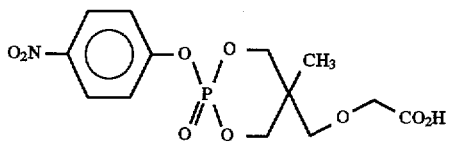

To a solution of ester 11 (10.1 g, 26.9 mmol, less soluble isomer) in 160 ml THF there is added 100 ml methanol followed by the dropwise addition of a solution of potassium carbonate (4.20 g, 30.4 mmol) in 50 ml water (addition time is 15 m). Another 100 ml water is subsequently added over a 5 m period. After stirring at RT for 90 m the reaction mixture is poured in 750 ml water. Extraction with 2×300 ml toluene, followed by washing the toluene layers with 150 ml water, drying and evaporation gives 2.96 g of the starting ester 11. The combined aqueous layers are acidified with about 6 ml conc. hydrochloric acid, then extracted with 3×300 ml toluene. Drying and rotary evaporation of these toluene layers gives a solid residue which is stirred with some ether.

Filtration and washing with ether gives 4.70 g of the acid 12 (13.0 mmol, 48% yield). $^1$H-NMR (CDCl$_3$/DMSO-d$_6$) :δ0.95 (s, 3H), 3.7 (s, 2H), 3.9–4.6 (m) and 4.05 (s) (6H), 7.2–8.2 (AB, 4H).

An attempt to hydrolyse the more soluble isomer of 11 obtained above using lithium hydroxide led to complete hydrolysis of the phosphate ester.

2-[[5-methyl-2-[(4-oxo-1,2,3-benzotriazin-3(4H)-yl) methyl-thio]-1,3,2-dioxaphosphorinan-5-yl,2-sulfide]] methoxyacetic acid 13 (azinphos hapten)

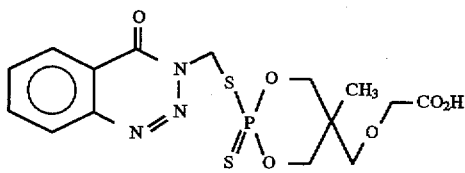

To a suspension of the bispotassium salt 6 (8.71 g, 25.03 mmol) in 100 ml methanol there is added conc. hydrochloric acid (2.93 g, d 1.172, 27.7 mmol), followed by 20 ml water. The resulting clear solution is evaporated completely. To the residue there is added 75 ml abs. ethanol and the mixture is stirred and warmed until a solution is obtained, 75 ml toluene is then added and the mixture is evaporated completely. 100 ml toluene is added to the residue and the mixture is rotary evaporated again. To the solid residue there is added 75 ml acetone, followed by 3-chloromethyl-1,2,3-benzotriazin-4(3H)-one (4.34 g, 22.2 mmol, prepared according to Chem Abstr 51 2888i). The mixture is stirred for 5 days at RT (the reaction is nearly complete after 2 days), then it is vacuum filtered, the solid salts being washed with some acetone. The filtrate is evaporated, the residue is stirred with a mixture of potassium carbonate (4.44 g, 32.17 mmol), 400 ml water and 400 ml toluene for 15 m. Water (250 ml) is added and the layers are separated. The aqueous layer is extracted with 250 ml toluene, the combined aqueous layers are acidified with about 9.5 ml conc. hydrochloric acid, and the product is extracted with 3×250 ml toluene, washed with 150 ml water, then dried and evaporated. This gives 6.67 g of acid 13 (15.5 mmol) as a viscous oil, which could not be made to crystallise. This product is stirred with 50 ml toluene, 2.4 g 40% dimethylamine in water (21.3 mmol), and so much methanol as is necessary for a clear solution. This solution is evaporated completely and the residue is stirred for 3 d with 75 ml toluene. The suspension is vacuum filtered and the solid is washed with some toluene to give 5.65 g of the dimethylamine salt of 13 (11:9 mmol, 47% yield based on 6). Dissolving a small amount of this salt in chloroform, washing this solution with some dilute hydrochloric acid and with water, drying and evaporation gives 13 as a viscous oil. $^1$H-NMR (CDCl$_3$) of 13 (1/1 mixture of isomers): δ0.9(s) and 1.25(s) (3H), 3.5(s) and 3.7(s) (2H), 3.8–4.6 (m, 6H), 5.7 (s) and 6.0 (s) (2H), 7.5–8.5 (m, 4H).

2-[[5-methyl-2-[2-(methylamino)-2-oxoethylthio]-1,3,2-dioxaphosphorinan-5-yl, 2-sulfide]]methoxyacetic acid 16 (dimethoate hapten)

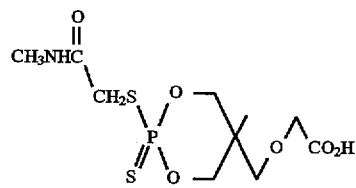

To a suspension of the bispotassium salt 6 (14.67 g, 42.16 mmol) in 200 mL methanol there is added 4.21 g concentrated hydrochloric acid (d 1.175, 40.5 mmol) followed by 30 mL water. The resulting solution is evaporated completely. Absolute ethanol (100 mL) is added and the suspension is warmed up to homogeneity, then evaporated completely. Toluene (100 mL) is added and the suspension is again evaporated. This latter step is repeated. Acetone (100 mL) is then added to the residue, followed by N-methyl-chloroacetamide (5.05 g, 46.98 mmol). The mixture is stirred for 3 days at RT, then evaporated. Potassium carbonate (8.80 g) in water (250 mL) is added to the residue followed by 250 mL toluene. After stirring for 15 m the layers are separated, the aqueous layer is extracted with 250 mL toluene, and the combined organic layers are washed with 100 mL water. To the combined aqueous layers there is added 17 mL concentrated hydrochloric acid, the resulting mixture is extracted with 3×200 mL chloroform. The chloroform layers are dried and evaporated to leave 8.2 g residue. Concentrated ammonia (5 mL) is added to this residue and the solution is evaporated completely. Acetone is added to the residue, the mixture is stirred and the resulting solid (the ammonium salt of 16) is filtered off and washed with acetone. This gives 2.77 g (1 isomer by NMR), which is dissolved in 100 mL water. Concentrated hydrochloric acid (2 mL) is added and the mixture is extracted with 3×100 mL chloroform. Drying and evaporation leaves a residue which on stirring with ether precipitates the pure acid 16. Filtration and washing gives 1.765 g (5.15 mmol, 12% based on 6). $^1$H-NMR (CDCl$_3$): δ 1.0 (s,3H), 2.8 (s) and 2.9 (s) (3H), 3.4 (s) and 3.7 (s)(2H), 3.6 (s,2H), 3.8–4.6 (m) and 4.1 (s)(6H), 6.5 (broad s, 1H), 9.3 (s, 1H).

(2-methoxy-5-methyl-1,3,2-dioxaphosphorinan-5-yl)methoxyacetic acid, methyl ester 14

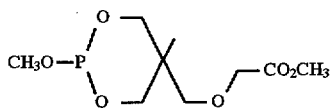

42 g (0.181 mol) of the acetal ester 2 is converted to diol 3 in the usual way using 200 mL methanol, 2.1 g pyridinium p-toluenesulfonate and 240 mL water. The resulting diol is stirred with 400 mL toluene, 33 g trimethylphosphite (0.266 mol) and 16 drops triethylamine for 3 days (see Edmundson, R. S; Johnson, O; Jones, D. W; King, T. J. *J. Chem. Soc., Perkin Trans. 2*, 1985, 69 for a similar procedure). After rotary evaporation at 300 mmHg and 40° C. the residue is washed with 2×100 mL water, then dried and evaporated. The residue is purified by bulb-to-bulb distillation at 0.1 mmHg to give 28.21 g of the pure product (0.112 mol 62%). $^1$H-NMR (CCl$_4$): δ 0.75 and 1.2 (ratio 2/1), 3.1–4.7 (m) with singlets at 3.3, 3.5, 3.6 and 4.0.

2-[2-(2,2-dichloroethenyloxy)-5-methyl-1,3,2-dioxaphosphorinan-5-yl,2-oxide]methoxyacetic acid 15 (dichlorvos hapten)

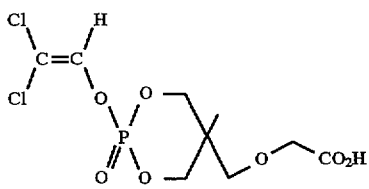

The phosphite 14 obtained above is dissolved in 150 mL toluene. With ice-cooling there is added 20.0 g chloral (0.136 mol) in 25 mL toluene in 15 m. The solution is stirred for 1 h at 0°–10° C. the 3 h at RT. The solution is completely evaporated, leaving as a residue the crude methyl ester of 15. $^1$H-NMR (CCl$_4$): δ 1.0 and 1.3 (s, 3H, ratio 1/2), 3.2–4.7 (m) and singlets at 3.3 3.7, 4.0 and 4.1 (11H), 7.0 (d, J=6, 1H). The crude ester is dissolved in a mixture of 100 mL THF and 150 mL methanol, then a solution of 15.0 g potassium carbonate (0.109 mmol) in 100 mL water is added in 10 m, another 100 mL water is added in 15 m, and the mixture is stirred at RT for 3 h. Water (500 mL) is added and the mixture is extracted with 2×250 mL chloroform. The organic layers are washed with 250 mL water. The chloroform layers contain impurities and starting ester. To the combined aqueous layers there is added 250 mL chloroform followed by 25 mL concentrated hydrochloric acid with stirring. The layers are separated and the aqueous layer is extracted with 2×250 mL chloroform. After drying and evaporation there is obtained 11.6 g of crude product which is stirred with 100 mL ether to give a colorless solid. Filtration and washing with ether affords 5.17 g of an unknown acid, not containing a vinyl proton by NMR, contamination with acid 15. Evaporation of the filtrate and stirring with some ether gives an additional 1.32 g of the unknown acid, contamination by some 15. Evaporation of the filtrate gives crude 15 which is dissolved in 25 mL methanol. Water (40 mL) is added dropwise with stirring, upon which pure 15 crystallises (the unknown acid is much more soluble in water/methanol than 15). Filtration and washing with water/methanol (3/1) gives 2.10 g (6.27 mmol, 6% based on the phosphite 14, mainly 1 isomer). Repetition of the latter procedure gives 1 isomer of 15. $^1$H-NMR (CDCl$_3$): δ 1.3 (s,3H), 3.4 (s, 2H), 3.8–4.8 (m) and 4.0 (s) (8H), 7.0 (d, J=5, 1H), 9.5 (broad s, 1H).

2-[[2-[2-(ethylthio)-ethylthio]-5-methyl-1,3,2-dioxaphosphorinan-5-yl,2-oxide]]methoxy-acetic acid 17 (demeton hapten)

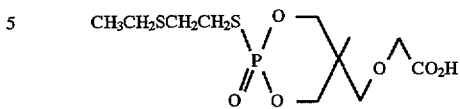

To an ice-cooled solution of ethylthioethanol (4.26 g, 40 mmol) in 50 mL THF there is added in 5 m 18 mL n-BuLi (ca. 2.25M in hexanes, 40.5 mmol). The suspension is stirred for 1 h at RT, then cooled with ice. The acid chloride 4 (mixture of isomers) (11.60 g, 40.2 mmol) dissolved in 15 mL THF is added in 10 m. The mixture is stirred overnight at RT, poured in 250mL water, and the product is extracted with 2×200 mL toluene. The combined toluene layers are washed with 3×100 mL water, then dried and evaporated. The residue, which slowly isomerises from the sulfide to the oxide at RT (this isomerisation can also be effected with trifluoroacetic acid, the resulting sulfide decomposes under our hydrolysis conditions), is dissolved in a mixture of 100 mL methanol and 100 mL THF. A solution of 5.50 g potassium carbonate (39.9 mmol) in 50 mL water is added in 10 m, followed by the addition of 100 mL water in 30 m. The solution is stirred for 3 h at RT, the poured in 500 mL water and extracted with 2×250 mL chloroform (some sodium chloride being added). The combined chloroform layers are washed with 2×100 mL water (some ethanol being added). The combined aqueous layers are acidified with 10mL concentrated hydrochloric acid, then extracted with 3×250 mL chloroform. After drying and evaporation a residue is obtained which is stirred in 50 mL toluene at RT for 10 days (this gives slow isomerisation from the sulfide to the oxide). The solution is evaporated and the residue is stirred for 2 d at RT with ether. This precipitates the desired 17 (1 isomer precipitates). Filtration and washing with ether affords 350 mg 17 (1.02 mmol, 2.5% based on acid chloride 4). $^1$H-NMR (CDCl$_3$): δ 1.0 (s, 3H), 1.3 (t,3H), 2.3–3.4 (m, 6H), 3.7 (s,2H), 3.9–4.6 (m) and 4.0 and 4.1 (s)(6H), 9.6 (1H).

4-benzyloxy-1-bromobutane 18

To a warm mixture of sodium hydroxide (240 g, 6 mol) in 260 mL water there is added benzylalcohol (174 g, 1.61 mol), 1,4-dibromobutane (624 g, 2.88 mol), 10 g aliquat 336, and 150 mL toluene with good stirring. The temperature of the reaction mixture rises slowly to about 60° C. and is kept below this temperature by slight cooling. When the temperature of the mixture drops the cooling bath is removed and the reaction mixture is stirred for an additional hour, then poured in 500 mL water. The product is extracted with 750 mL toluene and the organic layer is washed with 3×500 mL water, then dried, evaporated and purified by bulb-to-bulb distillation at 0,2 mmHg. This gives first 1,4-dibromobutane, then an intermediate fraction and then the product. After redistillation of the intermediate fraction there is obtained a total of 260 g of the product (1.07 mol, 66% yield, probably contaminated with some 1,4-dibenzyloxycompound) with bp 130° C. (0.2 mmHg). The product is used as such in the next step. $^1$H-NMR (CCl$_4$): δ 1.4–2.1 (m, 4H), 3.3 (2t, 4H), 4.3 (s, 2H), 7.2 (s, 5H).

2-(4-benzyloxy)butyl-propanedioic acid, diethyl ester 19

To a warm solution of sodium (49.5 g, 2.15 mol) in 1 L abs. ethanol there is added diethyl malonate (325 mL, 2.11 mol). The solution is warmed up to 50° C. and crude bromide 18 (410 g, 1.68 mol) is added over a 30 m period. The mixture warms up to 65° C. and is then heated under reflux for 1 h. Most of the solvent is evaporated and to the residue there is added 1 L toluene and 500 mL water. The layers are separated and the organic layer is washed with 2×750 mL water, then dried and evaporated. The residue is purified by bulb-to-bulb distillation to afford 410 g of 19 (1.273 mol, 76%) with bp 170° C. (0.2 mmHg). This product is used as such in the next step. $^1$H-NMR (CCl$_4$): δ 1.0–2.0 (m) and 1.2 (t) (12H), 3.2(t, 1H), 3.4 (t, 2H), 4.0 (q, 4H), 4.3 (s, 2H), 7.2 (s, 5H).

2-(4-benzyloxy)butyl-1,3-propanediol 20

The crude 19 obtained above is dissolved in 200 mL ether and then added over a 3 h period to a mixture of lithium aluminium hydride (66.7 g, 1.755 mol) and 1 L ether (the temperature of the reaction mixture is kept below 30° C. by external cooling). The mixture is stirred overnight at RT, then heated under reflux for 1 h. The excess of the hydride is decomposed by the slow addition of 20 mL ethyl acetate, followed by 20 mL methanol and 100 mL conc. hydrochloric acid, all with cooling. Hydrochloric acid (5N, 1 L) is then added and the mixture is stirred until two clear layers result. The layers are separated and the aqueous layer is extracted with 2×500mL ether. The combined ether layers are washed with 500 mL water, then dried and evaporated. The residue is used as such in the next step. $^1$H-NMR (CDCL$_3$): δ 1.0–2.0 (m, 7H), 3.2–3.8 (m, 8H), 4.4 (s, 2H), 7.2 (s, 5H).

5-(4-benzyloxy)butyl-2,2-dimethyl-1,3-dioxane 21

To the crude diol 20 obtained above there is added 500 mL 2,2-dimethoxypropane and 5 g p-toluenesulfonic acid. The mixture is stirred overnight at RT, then 10 g potassium carbonate is added and the mixture is evaporated. To the residue there is added 500 mL toluene and the solution is washed with 500 mL dilute sodium bicarbonate solution and with 500 mL water. The aqueous layers are extracted with 500 mL toluene. The combined toluene layers are dried and evaporated. The residue is purified by bulb-to-bulb distillation to give 21 (322 g, 1.158 mol, 86% yield based on diester 19) with bp 140° C. (0.2 mmHg). It is used as such in the next step. $^1$H-NMR (CCl$_4$): δ 1.0–1.9 (m) and 1.3 (s) (13H), 3.1–3.9 (m, 6H), 4.3 (s, 2H), 7.2 (s, 5H).

5-(4-hydroxybutyl)-2,2-dimethyl-1,3-dioxane 22

A mixture of the crude 21 obtained above (161 g, 0.579 mol), 300 mL acetic acid and 10 g 10% palladium on carbon is hydrogenated at 1 atm until the NMR of a sample showed the absence of the benzyl group. The mixture is then filtered, washed with acetic acid and evaporated. NMR of the residue indicated that the material had undergone considerable deprotection. The crude product is therefore stirred overnight with 250 mL 2,2-dimethoxypropane, 50 mL acetone and 3 g p-toluenesulfonic acid. Potassium carbonate (10 g) is added, the mixture is stirred for 1 h, then filtered and evaporated. The residue is purified by bulb-to-bulb distillation to afford 85.0 g of 2.22 (0.452 mol, 78%) with bp 110° C. (0.2 mmHg). $^1$H-NMR (CDCl$_3$): δ 0.9–2.0 (m) and 1.4 (s) (13H), 2.7 (bs, 1H), 3.3–4.1 (m, 6H).

5-(4-cyanobutyl)-2,2-dimethyl-1,3-dioxane 23

The alcohol 22 obtained above (85.0 g, 0.452 mol) is dissolved in 350 mL toluene and then added to a solution of 120 g sodium hydroxide in 150 mL water. Phase-transfer catalyst (aliguat-336, 5.5 g) is added, followed by the addition of p-toluenesulfonyl chloride (110 g, 0.577 mol) over a 30 m period with good stirring (temperature kept below 25° C. by ice-cooling). After stirring overnight the mixture is poured in 500 mL water and 200 mL toluene. The organic layer is separated and the aqueous layer is extracted with 250 mL toluene. The organic layers are washed with 500 mL water, then dried and evaporated to give the crude tosylate. $^1$H-NMR of the tosylate (CCl$_4$): δ 0.9–1.9 (m) and 1.2 (s) (13H), 2.4 (s, 3H), 3.1–4.1 (m, 6H), 7.0–7.7 (AB, 4H).

This tosylate is dissolved in 250 mL DMSO, sodium cyanide (29.4 g, 0.60 mol) is added and the mixture is heated at 90°–100° C. for 2.5 h. After cooling, the mixture is poured in 500mL water and the product is extracted with 2×250 mL toluene. The toluene layers are washed with 300 mL water, then dried and evaporated. The residue is purified by bulb-to-bulb distillation to give the nitrile 23 (79 g) 0.401 mol, 82% yield based on alcohol 22) with bp 120 (0.2 mmHg). $^1$H-NMR (CCl$_4$): δ 0.9–1.9 (m) and 1.3 (s) (13H), 2.2 (t, 2H), 3.1–3.9 (m, 4H).

5-(2,2-dimethyl-1,3-dioxan-5-yl)pentanoic acid, methyl ester 24

The crude nitrile 23 obtained above (79 g, 0.401 mol) is heated under reflux for 24 h with potassium hydroxide (31 g, 0.47 mol), 250 mL ethanol and 100 mL water. 300 mL water is added and most of the ethanol is distilled off. 200 mL n-propanol is added and the mixture is heated under reflux for 2 d. After cooling, 300 mL water is added and the mixture is extracted with 2×250 mL toluene. The toluene layers are washed with 250 mL water. The aqueous layers are evaporated, the last traces of water are removed at 100° C. (0.2 mmHg). The solid residue is stirred for 24 h with 300 mL DMF and 62 mL dimethyl sulfate (0.66 mol). The mixture is evaporated and to the residue there is added 500 mL toluene and 300 mL water. The layers are separated and the toluene layer is washed with 300 mL water. The aqueous layers are extracted with 250 mL toluene. The combined organic layers are dried and evaporated end the residue is purified by bulb-to-bulb distillation to give ester 24 (47.7 g, 0.207 mol, 52%) with bp 120° C. (0.2 mmHg). $^1$H-NMR (CCl$_4$): δ 1.0–1.9 (m), 1.25 (s) and 1.30 (s) (13H), 2.2 (bt, 2H), 3.2–3.9 (m) and 3.6 (s) (7H).

7-hydroxy-6-hydroxymethyl-heptanoic acid, methyl ester 25

To a solution of ester 24 (8.0 g, 34.8 mmol) in 50 mL methanol there is added 0.52 g pyridinium p-toluenesulfonate, followed by 60 mL water (added in 1 h). The solution is stirred for 3 h, then evaporated completely. 50 mL toluene is added and the mixture is evaporated completely. The residue is used as such in the next step. $^1$H-NMR (CDCl$_3$): δ 1.0–1.9 (m, 7H), 2.3 (bt, 2H), 3.3–3.8 (m) and 3.6 (s) (9H).

5-[2-(4-nitrophenoxy)-1,3,2-dioxaphosphorinan-5-yl, 2-sulfide]pentanoic acid (parathion hapten) 26

To the crude diol 25 obtained above there is added 75 mL toluene and 10 mL pyridine (0.124 mol) followed by O-(4-nitrophenyl)-phosphorodichloridothioate (9.4 g, 34.6 mmol) (prepared according to H Tolkmith, J Org Chem 23 1685 (1958)) causing a slightly exothermal reaction. The suspension is stirred for 40 h, then poured in 250 mL water and 200 mL toluene. The layers are separated and the organic layer is washed with 2×200 mL water containing some sodium chloride, then dried and evaporated to give 12.8 g of the crude methyl ester of 26. $^1$H-NMR (CDCl$_3$): δ 1.0–1.9 (m, 7H). 2.3 (t, 2H), 3.6 (s, 3H), 3.9–4.7 (m, 4H), 7.1–8.2 (AB, 4H).

The ester is dissolved in 150 mL THF, 100 mL methanol is added followed by the addition of potassium carbonate (5.00 g, 36.2 mmol) in 50 mL water over a 5 m period. Another 100 mL water is added in 5 m, then the solution is stirred for 64 h. 300 mL water is added and the mixture is extracted with 2×250 mL chloroform. The chloroform layers are washed with 150 mL water, then dried and evaporated. According to NMR this residue is almost pure starting ester. The aqueous layers are combined and acidified with 9 mL conc. hydrochloric acid, then extracted with 3×100 mL chloroform. Drying and evaporation leaves a solid residue which is stirred with ether, then filtered. The solid is recrystallised from toluene to give 1.67 g of 26 as a mixture of the 2 isomers.

The ether and toluene filtrates are combined, evaporated and the residue is combined with the recovered ester mentioned above. This material is stirred with a mixture of THF, methanol and potassium carbonate (10.0 g, 72.5 mmol) in water for 24 h. Workup as above gives again some starting ester, whereas from the aqueous layer there is obtained, after acidification and extraction, the crude acid 26. Stirring with ether gives 1.57 g of pure 26 for a total yield of 3.24 g (8.64 mmol, 25% yield based on ester 24). $^1$H-NMR (CDCl$_3$): δ 1.1–2.0 (m, 7H), 2.35 (2t, 2H), 4.0–4.4 (m, 2H), 4.3–4.7 (AB, 2H) 7.2–8.3 (AB, 4H), 10.0 (bs, 1H).

C. PREPARATION OF IMMUNOCONJUGATES

As stated previously, small molecules such as organophosphate pesticides cannot by themselves induce an immune response when injected into animals. However by conjugating haptens containing a functional group with a suitable linker arm to immunologically active proteins, antibodies can be generated which recognise and react with the hapten molecule.

Accordingly, in a further aspect, the present invention provides immunoconjugates suitable for use in raising antibodies. Such immunoconjugates comprise the compounds of formula (I) or formula (IV) coupled to an appropriate macromolecule such as a protein. Any protein macromolecule conventionally used in the art for this purpose can be employed, with bovine serum albumen, mouse albumen, polylysine and ovalbumen being useful examples.

Any suitable method can be used to form the immunoconjugates of the invention. By way of illustration, three methods wellknown in the art and commonly used to conjugate haptens containing a carboxyl group to proteins are:
(i) the mixed anhydride method (Marks et al in "Enzyme-Linked Immunoassay of Hormones and Drugs" (S B Pal Ed) p 419 Walter de Gruyter, Berlin (1978));
(ii) carbodiimides (CDI) (Erlanger, Methods in Enzymology 70 85 (1980)); and
(iii) the N-hydroxy succinic ester (NHS) method (Gros et al Prot Biol Fluids Proc Coll 24 763 (1976)) which is a variant of the CDI procedure.

In practising the invention, method (iii) is preferred by the applicants because of its greater efficiency and ease of control of reaction. This procedure is generally as follows: The hapten of formula (I) is reacted with a CDI (e.g. N-ethyl -N''-(3'-dimethylaminopropyl) carbodiimide hydrochloride, EDC) and N-hydroxy succinimide (NHS) to form the succinimidyl ester of the hapten. The ester is then reacted with amino groups on the protein to form the immunoconjugate.

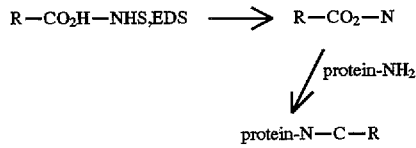

A specific non-limiting example of the conjugation procedure is set out below.

C.1 Procedure:
1. Dissolve the hapten (0.2 mM) in 1 ml of diethylformamide (DMF). Add 30 mg of NHS and 40 mg of EDC. Stir for 2 hours at room temperature.
2. Dissolve Bovine serum albumen or ovalbumen (20 mg) in 0.6 ml of distilled water and add 0.4 ml of DMF in a stirred reactivial (Pierce Chemicals).
3. Add 0.050 ml of the hapten -NHS ester to the protein solution and incubate overnight.
4. Dialyse exhaustively against distilled water.
5. Measure the concentration of protein (Bradford Analytical Biochemistry 72 248 (1976)) and phosphorous (Atomic adsorption spectroscopy) to determine the moles of hapten/ mole of protein.

Using this procedure, immunoconjugates comprising the chlorpyrifos hapten 8, the parathion hapten 10, the paraoxon hapten 12, the azinphos hapten 13 and the demeton hapten 17 with ovalbumen were prepared with the degree of coupling being between 8 and 50 moles of hapten/mole of ovalbumen. These immunoconjugates were used in the production of antisera as described below.

Immunoconjugates were also prepared using the same procedures but substituting BSA for ovalbumen-these conjugates were used for all immunoassays as the capture antigen.

D. ANTIBODY PRODUCTION

Production of Organophosphate-specific Antibodies

Having formed immunoconjugates comprising the compounds of formula (I) coupled to a protein macromolecule, a further aspect of the invention provides for the production of antibodies to such immunoconjugates. Antibodies can be in the form of antisera containing polyclonal antibodies, or monoclonal antibodies may be obtained by use of hybridoma technology. Still further, the antibodies or fragments can be produced using recombinant DNA techigues.

Where it is desirable to obtain polyclonal antibodies or binding fragments of such antibodies, any conventional immunisation protocol can be employed. An example of such a protocol is given below in relation to the chlorpyrifos, parathion, paraoxon, demeton and azinphos immunoconjugates prepared as specifically described above in Section C.

In the alternative, where it is desirable to obtain monoclonal antibodies or binding fragments of such antibodies, the procedure of Kohler and Milstein (Kohler G and Milstein C, "Continuous Cultures of Fused Cells Secreting Antibody of Predefined Specificity", Nature 256 495–497 (1975)) can be used. Generally, this procedure involves the immunisation of an animal with the immunoconjugate, obtaining antibody-producing cells from the animal and fusing the antibody-producing cells with strains of myeloma cells to produce hybridomas. These hybridomas are grown or cultured to produce monoclonal antibodies specific for the organophosphate portion of the immunoconjugate.

An example of the procedure which can be employed to obtain hybridomas secreting monoclonal antibodies of the appropriate specificity is given below in relation to the parathion and azinphos immunoconjugates described above.

Finally, procedures by which antibodies or binding fragments can be produced recombinantly are detailed in Section D3 below.

D.1 Production of Polyclonal Antisera

Balb c×DBA mice (4 per hapten) were immunized with 200 μg of ovalbumen conjugate in 50% Freunds incomplete adjuvant, at subcutaneous and intraperitoneal sites, and rested for 4 weeks. Three booster injections (100 μg conjugate in 50% incomplete Freunds adjuvant), were given at 3 weekly intervals. Sera were isolated from blood taken prior to immunization (PI control) and at 8–10 days after immunization.

Sera were stored at −20° C.

D.2 Production of Monoclonal Antibodies (MAbs)

For preparation of MAbs, mice (Balb/c PN×DBA) were injected with ovalbumin/hapten immunoconjugates as described above. Prior to fusion mice were rested for a minimum of four weeks.

Four days prior to fusion, mice were immunised, intraperitoneally, with 500 μg of immunoconjugate. Spleen cells were prepared and fused with murine myeloma cell line, preferably P3-NS-1-Ag4-1, using polyethylene glycol. The fusion protocol, culture and cloning procedures were as described in Jones W T, Reynolds P H S, Jones S D, Liddane C P Land Rodbur K A, *Plant Physiology* 94: 1358–1364 (1990). Monoclonal cultures of hybridomas (Spleen/myeloma fused cells) were stored in liquid nitrogen.

Monoclonal antibodies were prepared in mg quantities from the culture fluid in which the hybridomas were grown or in g quantities from either ascitic tumours or an in house in vitro hollow fibre culture system.

D.3 Production of Antibody Fragments

Antibody fragments can be prepared by controlled protease digestion of whole immumoglobulin molecules as described in Tjissen P, "Practice and theory of enzyme immunosays" in Laboratory techniques in Biochemistry and Molecular Biology, Elsevier Amsterdam, New York, Oxford, 117–121 (1990).

Alternatively, antibody fragments can be prepared using molecular biological techniques by isolating, from hybridoma cells, the genetic material encoding the variable regions of the heavy, light or beth chains of the monoclonal antibodies and expressing them in suitable organisms for the production of recombinant antigen binding fragments (Fv, ScFv, Fab etc.) of the monoclonal antibody (Hodgson J, "Making monoclonals in microbes", *Biotechnology* 9 4231–425 (1991).

E. IMMUNOASSAY PROCEDURES AND RESULTS THEREOF

As indicated above, the immunoconjugates of the invention comprise an organophosphate functional group with a linker arm coupled to an immunologically active protein macromolecule.

The nature of the linker arm and its position on the organophosphate hapten molecule will affect the specificity of the antibody and the ability of the free hapten to react with the antibody, although invariably the hapten-protein immunoconjugate does react with the antibody. Antibodies generated to hapten-protein immunoconjugates must therefore be tested to show if they react with the free hapten, parent organophosphate as well as the immunoconjugate, and for specificity i.e. do they also react with small molecules having some of the common structural features found in the hapten used for immunisation.

E.1 Polyclonal Antibodies (a) Testing of Polyclonal Antisera for Antibodies to Haptens 96-well polystyrene plates were coated with BSA-conjugates by incubation in solutions of conjugates (4 μg/ml in phosphate-saline buffer (PBS, pH 7.0)) for 2 hrs at 37° C. Plates were blocked with 2% BSA in PBS, overnight at 4° C.

Sera (PI control+final bleeding) were serially diluted (½ dilution starting 1/100) in 2% BSA/PBS+0.1% Tween 20 (1 hr 37° C.) followed by incubation with peroxidase labelled sheep antimouse Ig (γ chain specific). Bound peroxidase was measured by incubation of wells with substrate solution (orthophenylene diamine, OPD, 40 mg per 100 ml of citrate phosphate buffer pH 6.0 containing 0.003% hydrogen peroxide). The reaction was stopped after 30 mins by addition of 4M sulphuric acid, and absorbance at 492 nm was measured on a Flow Multiscan MC microwell plate reader.

(b) Competition Assay

Conditions for ELISA were as described above in Section E.1(a). Checkerboard titrations of antisera and hapten-BSA were carried out for each sera. Optimal plating antigen and serum dilution were taken as primarily the lowest sera concentration and secondly the lowest antigen concentration (non saturating conditions) to give a final signal at 492 nm in the range 0.8–1.200 units. Microwell plates were coated at the optimal BSA hapten concentration.

Organophosphate pesticides and haptens were dissolved in methanol at 2 mg/ml. Serial dilutions were made in methanol from 2000→0.3 μg/ml. One tenth dilutions of organophosphate and methanol (O control) were made into 2% BSA/PBST (200 μg→3.0 ng/ml). Equal volumes of each organophosphate and sera at 2× optimal concentration in 2% BSA, PBST were mixed and incubated at 37° C. for 2 hrs. Aliquots (100 μl) were added to the microwell plate and incubated for 1 hr, followed by peroxidase antimouse and substrate as described above.

For calculation of the results, the transformation:

$$\frac{B_o - B}{B_o} \times 100\%$$

where $B_o = OD^{490nm}$ in absence of competing species (i.e. methanol)

$B = OD^{490nm}$ in presence of competing species was plotted against log of concentration of competing species. $I_{50}$, the concentration of competing species to inhibit binding by 50%, and $I_{20}$ and $I_{80}$, the concentration to give 20% and 80% inhibition were determined graphically from each plot.

E.2 Monoclonal Antibodies (a) Screening of Cultures for Monoclonal Antibodies to Hapten Immunoconjugates Screening was carried out by an ELISA using 96 well plates (Maxisorb, Nunc) coated with BSA/hapten conjugates and blocked with BSA. Culture fluid, diluted up to 3000× in dilution buffer (PBST, 2% BSA phosphate buffered saline containing 0.1% Tween 20 and 2% BSA), was added to the coated plates for 2 hours at 37° C. The plates were washed 6× with PBST, flicked dry and incubated for 1 hour with peroxidase labelled antibodies raised in goats against mouse IgG (Sigma chemicals A3673, γ chain specific).

Positive cultures were detected following the addition of peroxidase substrate (ortho phenylene diamine (OPD)) by measurement of the absorbance at 492 nm.

(b) Competitive ELISA to Identify Hybridoma Cells Recognising Organophosphate Pesticides Cultures secreting antibodies recognising hapten immunoconjugates were further tested by an ELISA procedure to identify cultures recognising the "native" organophosphate pesticide.

Optimal BSA/hapten immunoconjugate plating concentration and dilution of culture fluid was determined by chequerboard titrations for each culture. The optimal plating concentration of conjugate was taken to be the highest dilution of immunoconjugate to achieve non saturating conditions. The optimal antibody concentration was the dilution of culture fluid to give a final absorbance at 492 nm of approximately-1.0 at the optimal plating immunoconjugate concentration with peroxidase anti-mouse IgG and substrate concentrations as described above.

96 well ELISA plates were treated with the optimal concentration of BSA/hapten immunoconjugate, and remaining protein binding sites on the wells were blocked with 2% BSA.

Culture fluids were diluted to 2× the determined optimal dilution. Organophosphate pesticide was dissolved in 2%

BSA in PBST containing 10% MeOH, to a concentration corresponding to 2× to give 50% inhibition (2×I$_{50}$) when serum, prepared from the blood of the mouse used for the preparation of hybridomas, was used as the antibody.

Equal volumes of organophosphate pesticide or 10% MeOH (negative control) and diluted culture fluid were mixed and incubated at 37° C. for 2 hours and 0.1 ml of the mixture was added to the coated ELISA wells for a further 2 hours at 37° C. Plates were washed and reacted with peroxidase-labelled goat anti-mouse IgG and developed with substrate as described above. The absorbance at 492 nm was compared for culture fluid in MeOH and organophosphate pesticide mixtures. Reduction in $A^{492nm}$ in the presence of organophosphate pesticide was observed for cultures containing antibodies recognising native organophosphate pesticide.

(c) Subclass Determination of Monoclonal Antibodies

Subclass and light chain (k or λ) was determined for each antibody recognising native organophosphate pesticide, using an antigen-capture ELISA in combination with the Biorad isotyping kit (ref) used according to the manufacturer's recommendations.

(d) Competitive Assays and Cross-Reactivity of MAbs with other Organophosphate Pesticides and Synthetic Intermediates Optimum conditions for competitive ELISA were determined as described above, using peroxidase-labelled MAbs recognising parathion and azinophos pesticides. The assay involved a solid surface coated with BSA-hapten and the peroxidase-labelled antibodies as the detecting molecules. Those skilled in the art will recognise that other competitive assay formats are also possible.

The competing analyte was tested in the concentration range 300 pg to 0.2 mg/ml. Antibodies from three different clones were tested in assays for parathion (4D4, 8B1, 10H12) and azinphos (7E10, 8G8, 9D11).

E.3 Purification and Labelling of Monoclonal Antibodies

Monoclonal antibodies (MAb) were purified by ammonium sulphate fractionation and affinity chromatography on protein A sepharose. The antibodies can be labelled with any of a number of different enzymes using one of several procedures (P Tijssen, In "Laboratory techniques in Biochemistry and Molecular Biology", *Practice and Theory of Enzyme Immunoassays* 151–278, ISBN 0-7204-4200-1, Elsevier, Amsterdam, New York, London (1990)). As an example, monoclonal antibodies were labelled with horseradish peroxidase using the heterobifunctional reagent N-Succinimidyl-3-(2-pyridyl-dithio) propionate (SPDP) as modified from previously published methods (P Nilsson, N R Berquist and M S Grundy, *J Immunological Methods* 41, 81 (1981)).

Peroxidase and MAb were treated with SPDP for 40 min at 23° C. Excess SPDP was removed by gel filtration and the modified peroxidase was reduced by treatment with dithiothreitol (DTT). The peroxidase and modified MAb were reacted overnight at 23° C. Peroxidase-labelled MAb was purified from excess peroxidase by ammonium sulphate fractionation (50% saturated ammonium sulphate) and gel filtration and stored in aliquots at −20° C.

E.4 Anti-Cholinesterase Activity of Haptens and Organophosphate Pesticides

Organophosphate pesticides and their haptens were tested for ability to inhibit cholinesterase activity using a pesticide biosensor detector kit (Enzytec Inc, Kansas City, Mo., USA. The lowest concentration to inhibit a positive reaction was determined for each test molecule using the manufacturer's protocol).

E.5 Results

E.5.1 Polyclonal

Ovalbumen immunoconjugates of chlorpyrifos, parathion, paraoxon, demeton and azinphos haptens injected into mice resulted in the production of antisera recognising haptens conjugated to BSA. No reaction was observed when preimmune sera were reacted with BSA-haptens or when sera from immunized mice were tested against BSA. Thus a specific reaction to the hapten was apparent.

Serum titres for mice immunized with chlorpyrifos immunoconjugate ranged from 1/20,000 to 1/160,000; parathion immunoconjugate 1/640,000–1/1,200,000; for paraoxon immunoconjugate 1/320,000–1/1,200,000; for azinphos immunoconjugate 1/640,000–1/2,400,000; and for demeton immunoconjugate 1/256,000–1/2,400,000.

Optimal plating concentrations for BSA-hapten, and sera dilution to give absorbance 0.8–1.2 were:

(a) chlorpyrifos hapten: BSA-hapten 1/160,000 to 1/640,000; sera dilution 1/16,000–1/64,000;

(b) parathion-hapten: BSA-hapten 1/320,000–1/640,000 sera dilution 1/32,000–1/64,000;

(c) paraoxon hapten: BSA-hapten 1/80,000–1/640,000; sera dilution 1/8,000–1/32,000;

(d) azinphos hapten: BSA-hapten 1/640,000–1/1,200,000; sera dilution 1/64,000;

(e) demeton hapten: BSA-hapten 1/80,000–1/640,000; sera dilution 1/32,000–1/128,000.

Competition, defined as the inhibition of binding of antibody to microwell plates as a result of incubation with organophosphate pesticide or hapten, was observed for all mice and all pesticides. Within a particular assay, variation was observed between mice in the $I_{50}$ and in the useful range ($I_{20}$–$I_{80}$) for measuring of organophosphate, with specific results as follows.

(a) Chlorpyrifos immunoconjugate

Using optimal conditions outlined above, sera from mice resulted in competition. Parameters $I_{50}$=300 ng/ml, $I_{20}$=60 ng/ml, $I_{80}$=1500 ng/ml for mouse 1 and 2 for chlorpyrifos. Mouse 3 and 4 $I_{50}$=150 ng/ml $I_{20}$=25 ng/ml $I_{80}$=860 ng/ml. Competition was not measurable at concentrations of paraoxon, parathion and azinphos methyl up to 100 µg/ml. The chlorpyrifos hapten had $I_{50}$ of 20 ng/ml. $I_{20}$=1 ng/ml and $I_{80}$=100 ng/ml for all mice.

(b) Parathion immunoconjugate $I_{50}$, $I_{20}$ and $I_{80}$ for parathion using mouse 1 serum were 1.2 µg/ml, 80 ng/ml, 16 µg/ml; mouse 2 serum, 800 ng/ml, 60 ng/ml, 11 µg/ml; mouse 3 serum, 4 µg/ml, 300 ng/ml, 31 µg/ml and mouse 4 serum 2.1 µg/ml 350 ng/ml and 33 µg/ml respectively. For all mouse sera, no competition was observed with chlorpyrifos and azinphos; Paraoxon showed cross reactivities of 0.6% and 0.4% for mouse 1 and 2 respectively and no cross reaction for mouse 3 and 4 sera. Competition with parathion hapten gave $I_{50}$'s 20–25 ng/ml, $I_{20}$ 1–2 ng/ml, $I_{80}$ 80–100 ng/ml.

(c) Paraoxon immunoconjugate $I_{50}$, $I_{20}$ and $I_{80}$ for paraoxon using mouse 1 serum was 8.1 µg/ml, 1.2 µg/ml and 46 µg/ml; for mouse 2, 2.2 µg/ml, 710 ng/ml, and 105 µg/ml, for mouse 3 serum 8 µg, 1.2 µg/ml and 43 µg/ml, and mouse 4, 2 µg/ml 200 ng/ml and 23 µg/ml respectively. No cross reaction was observed for any sera, from mice injected with paraoxon-hapten immunoconjugates, with parathion, chlorpyrifos, or azinphos methyl or ethyl. The paraoxon hapten gave an $I_{50}$ of 20 ng/ml and $I_{20}$ of 2 ng/ml and $I_{80}$ of 100 ng/ml.

(d) Azinphos immunoconjugate $I_{50}$, $I_{20}$ and $I_{80}$ for azinphos methyl using mouse 1 and 3 sera were 4 µg/ml, 400 ng/ml and 30 µg/ml, for mouse 2 serum, 20 µg/ml 800 ng/ml and 120 µg/ml, for mouse 4 serum 800 ng/ml, 20 ng/ml, 34 µg/ml. Chlorpyrifos and paraoxon showed no cross reaction. Parathion showed cross reaction at 1–2% of azinphos methyl. Azinphos ethyl was slightly more competitive than azinphos methyl. For the azinphos hapten $I_{50}$ ranged from 6–10 ng/mls, $I_{20}$ 1–2 ng/ml and $I_{80}$ of 60–100 ng/ml.

(e) Demeton immunoconjugate $I_{50}$, $I_{20}$ and $I_{80}$ for demeton using mouse 1 and mouse 4 sera were 20 µg/ml, 800 ng/ml and 120 µg/ml; for mouse 3 was 66,7 and 400 µg/ml; for mouse 2 was 200,18 and 800 µg/ml.

E.5.2 Monoclonal

Fusions were carried out to obtain MAbs recognising (a) Parathion (b) Azinphos methyl.

For Azinphos, 120 cultures (12% of culture wells) were obtained which contained hybridomas secreting antibodies recognising hapten immunoconjugates. Of these 12 cultures also recognised free azinphos methyl. Two of these cultures gave greater than 80% inhibition, eight gave approximately 50% inhibition (equivalent to polyclonal antibodies present in the serum of the mouse used in the fusion) and two gave 30% inhibition. All MAbs were mouse IgG1 k light chain.

For parathion, 225 cultures (19% of wells) contained hybridoma cells recognising hapten immunoconjugates, 13 of which also recognised free parathion. Seven of these cultures gave 50% inhibition (equivalent to serum polyclonal antibodies) and the remaining six cultures gave 30% inhibition. For further studies, 3 cell lines secreting MAbs to each of parathion and azinphos were selected.

E.5.3 Competitive Assays and Cross Reactivity of MAbs with other Pesticides and Synthetic Intermediates The solid phase was coated with the hapten conjugated to BSA. Labelled antibody was incubated with the competing analyte (300 pg–0.2 mg/ml) and 0.1 ml added to the coated wells. Peroxidase-labelled antibody bound to the solid phase was determined (using ortho phenylene diamine (OPD) in citrate/phosphate buffer pH 5.0 as substrate) spectrophotometrically on a Dynatech MR5000 plate reader. Any other suitable substrate could be used instead of OPD.

Results for three MAbs raised against the parathion immunoconjugates and three against the azinphos immunoconjugate are shown in Tables 2 and 3 respectively.

MAbs prepared against the parathion and azinphos immunoconjugate could be used to quantitate parathion and azinphos methyl in ng to low µg/ml and in the picogram to low ng range respectively under the assay conditions given here. Sensitivity could be increased by varying assay conditions, and the nature of the detection label.

When MAbs raised against the parathion immunoconjugate were used, only parathion and closely related pesticides could be detected. MAbs 4D4 and 8B1 could not be distinguished in terms of specificity or sensitivity. Thus both detected parathion and to a lesser degree both fenitrothion (30%) and paraoxon (2%) but showed no detectable reaction with 4-nitrophenol or other organophosphates tested. MAb 10H12 detected fenitrothion (80%) and paraoxon (100%) but otherwise had similar specificity to 4D4 and 8B1.

MAbs 7E10, 8G8 and 9D11 all showed similar specificity, reacting to azinphos methyl and to a lesser degree closely related azinphos ethyl (30%) and synthetic intermediates used in the preparation of the azinphos hapten (<0.01%). Other organophosphates showed no detectable reaction (<0.003%).

TABLE 2

Reaction[a] of monoclonal antibodies raised against parathion immunoconjugate with pesticides and related compounds

| COMPOUND | ANTIBODY | | |
|---|---|---|---|
| | 4D4 | 8B1 | 10H12 |
| Parathion[b] | 1.0 | 1.0 | 1.0 |
| Methyl parathion | 1.0 | 1.0 | 1.0 |
| Fenitrothion | 0.3 | 0.3 | 0.8 |
| Fenthion | <0.004 | <0.004 | <0.004 |
| Paraoxon | 0.02 | 0.02 | 1.0 |
| Parathion hapten[c] (unconjugated) | 100 | 100 | 100 |
| 4-nitrophenol | 0.004 | <0.004 | 0.004 |
| 2-(2-methoxy-5-methyl-1,3,2-dioxaphosphorinan-5-yl-2-sulphide)methoxyacetic acid-methyl ester | <0.004 | <0.004 | <0.004 |
| Azinphos methyl | <0.004 | <0.004 | <0.004 |
| Diazinon | <0.004 | <0.004 | <0.004 |
| Demeton | <0.004 | <0.004 | <0.004 |
| Chlorpyrifos methyl | <0.004 | <0.004 | <0.004 |
| Dimethoate | <0.004 | <0.004 | <0.004 |
| Dichlorvos | <0.004 | <0.004 | <0.004 |

[a]Data shown are the ratio of concentration of compound required to inhibit by 50% the binding of labelled MAb to coated antigen relative to the control pesticide parathion.
[b]The concentration of parathion to inhibit the reaction by 50% was 1.25, 1.25 and 0.4 micrograms/ml for 4D4, 8B1 and 10H12 respectively.
[c]Parathion hapten is 2-{5-methyl-2-(4-nitrophenoxy)-1,3,2-dioxaphosphorinan-5-yl,2-sulphide}methoxyacetic acid.

TABLE 3

Reaction[a] of monoclonal antibodies raised against azinphos immunoconjugate with pesticides and related compounds

| COMPOUND | ANTIBODY | | |
|---|---|---|---|
| | 7E10 | 8G8 | 9D11 |
| Azinphos methyl[b] | 1.0 | 1.0 | 1.0 |
| Azinphos ethyl | 0.3 | 0.3 | 0.3 |
| 2-(2-mercapto-5-methyl-1,3,2-dioxaphosphorinan-5-yl,2-sulphide)methoxyacetic acid bipotassium salt | 0.00012 | 0.00006 | 0.00006 |
| 3-hydroxymethyl-1,2,3-benzotriazin-4(3H0-one | 0.0003 | 0.0003 | 0.0001 |
| Azinphos hapten[c] (unconjugated) | 9.0 | 9.0 | 9.0 |
| Diazinon | <0.00003 | <0.00003 | <0.00003 |
| Parathion | <0.00003 | <0.00003 | <0.00003 |
| Chlorpyrifos | <0.00003 | <0.00003 | <0.00003 |
| Paraoxon | <0.00003 | <0.00003 | <0.00003 |
| Demeton | <0.00003 | <0.00003 | <0.00003 |
| Dichlorvos | <0.00003 | <0.00003 | <0.00003 |
| Dimethoate | <0.00003 | <0.00003 | <0.00003 |

[a]Data shown are the ratio of concentration of compound required to inhibit by 50% the binding of labelled MAb to coated antigen relative to the control pesticide azinphos methyl.
[b]The concentration of azinphos methyl to inhibit the reaction by 50% was 1.5, 0.3 and 2.0 nanograms/ml for 7E10, 8G8 and 9D11 respectively.
[c]The azinphos hapten is 2-[{5-methyl-2-{(4-oxo-1,2,3-benzotriazin-3(4H)-yl)methyl-thiol}-1,3,2-dioxaphosphorinan-5-yl,2-sulphide}]methoxyacetic acid.

E.5.4 Anti-Cholinesterase Activity of Haptens and Pesticides

Azinphos methyl and parathion showed inhibition of cholinesterase at concentrations greater than 0.3 and 2 ppm respectively. No inhibition was observed for their corresponding haptens at 200 ppm, the highest concentration tested using the Enzytec kit.

E.6 Discussion

All organophosphate haptens when conjugated to ovalbumen and injected into Balb c/DBA mice elicited a strong immune response resulting in antibodies of high titre to the corresponding BSA-hapten immunoconjugates. Furthermore, the sera indicated that a proportion of the antibody mixture recognised the parent organophosphate pesticide as well as the conjugated and unconjugated haptens. In all cases, under the conditions used, the unconjugated hapten was more effective in competing than was the parent pesticide indicating that the dioxane ring of the linker arm plays a role in the structure of the epitope recognised by the antibody.

The high degree of specificity of individual antibodies for the parent organophosphate pesticide also indicates that the specific part of the molecule (heterocyclic or aromatic ring) as well as the S=P or O=P also plays a major role in forming the epitope. Thus in the case of chlorpyrifos, neither parathion, paraoxon, azinphos methyl nor azinphos ethyl could compete at 100 µg/ml. Antibodies to paraoxon did not recognise parathion and a low cross reactivity (<4%) was observed for paraoxon with sera from mice immunised with parathion immunoconjugate. The structure of these pesticides differ only in regard to one atom, a divalent sulphur or divalent oxygen attached to the phosphorus atom. Azinphos-methyl showed ≅1.5% cross reactivity to parathion but no cross reaction to paraoxon. Thus the sulphur is a major aspect of the epitope recognised by antibodies raised to the parathion immunoconjugate.

Chlorpyrifos although also containing the S=P bond showed no cross reactivity to antibodies generated against parathion nor azinphos immunoconjugates.

Antibodies raised to the azinphos immunoconjugate showed no cross reaction to paraoxon nor chlorpyrifos. However ≅1–2% cross reaction was observed with parathion as the competing species. Azinphos methyl was only marginally less effective than azinphos ethyl in its ability to react with antibodies raised to the azinphos immunoconjugate.

The above results therefore indicate the suitability of the sera for use in immunoassay-based detection systems for detecting organophosphate pesticides.

The results also indicate that monoclonal antibodies can be selected to give assays of better sensitivity and differing specificity than the corresponding polyclonal sera.

This can be seen from the fact that assays which included MAbs to azinphos immunoconjugate as the detecting antibody resulted in approximately 200-fold increase in sensitivity compared to assays involving polyclonal sera. Also these MAb-based assays showed no cross-reactivity with parathion as did the sera-based assay.

Differences in specificity were found among the MAbs produced to parathion immunoconjugate. 10H12 reacted equally well with parathion and paraoxon, whereas the other MAbs 4D4 and 8B1 and the polyclonal sera showed only low levels of cross-reactivity to paraoxon.

The results therefore clearly indicate the suitability of the MAbs generated as described for use in immunoassay-based detection systems for detecting organophosphate pesticides.

It should be noted that the azinphos and parathion immunoconjugates showed no inhibition of cholinesterase activity at concentrations 200× in excess of levels found inhibitory for the parent organophosphates.

F. ORGANOPHOSPHATE DETECTION

In still a further aspect, the invention provides methods for quantifying the amount of organophosphate present in an environmental sample or biological product such as horticultural produce or foods. This quantification can be made using any of those immunological-based assay procedures known in the art (P Tijssen, In "Laboratory techniques in Biochemistry and Molecular Biology", *Practice and Theory of Enzyme Immunoassays* 151–278, ISBN 0-7204-4200-1, Elsevier, Amsterdam, New York, London (1990)).

By way of example, the procedure may comprise the steps of applying a sample suspected to contain the target organophosphate to an appropriate support with antibody or antibody fragments capable of specifically binding to the target organophosphate being bound to the support, and detecting any bound organophosphate/antibody complexes.

Any appropriate detection procedure may be employed to detect such complexes. Examples include an enzyme immunoassay step where an appropriate enzyme may be coupled to the antibody end subsequent substrate is added or radioimmunoassay, fluorescence immunoassay, chemiluminescence or agglutination detection steps.

Suitable supports for use in the assay include tubes, well plates, microplates, elongate sticks or thin strips or beads. These supports may be formed from materials such as plastics materials, nitrocellulose, nylon, glass or silica.

G. ASSAY KITS

In a further aspect, the invention provides kits for detecting and quantifying organophosphates in a sample. The critical component of such kits is a supply of antibody or antibody fragment specific for the particular target organophosphate.

Other components of assay kits known to those persons skilled in the art will usually also be included in the kits of the present invention. The identity of the additional components will to a great extent depend upon the type of assay involved and in particular upon the desired procedure by which the presence of target organophosphate is to be detected. Such components include a supply of the target organophosphate, a support to which either the antibody component or target organophosphate is or can be bound, the components of an enzyme-linked immunoassay detection system, and appropriate washing and blocking solutions.

It will however be usual for the assay kit to include a supply of immunoconjugate corresponding to the organophosphate to be detected.

H. ORGANOPHOSPHATE ISOLATION

In an additional aspect, the invention provides methods for isolating an organophosphate compound from a sample. Such samples include an environmental medium (such as water or soil).

In this method, the essential step of contacting the medium with the antibody differs little from that described for organophosphate detection and quantification. However, as the purpose of the method is isolation or removal of contaminant organophosphate compounds from the medium, the medium and the bound antibody/organophosphate complex require separation following the binding process. This separation can occur by physical removal of the antibody/organophosphate complex from the medium by removal of the support to which the antibody is bound. Alternatively, the separation can occur automatically where, for example, the environmental medium is water, by allowing the contaminated water to flow past the support to which the antibody is bound.

INDUSTRIAL APPLICABILITY

It can be seen that, at least in the preferred form of the invention, compounds of the formula (I) ("haptens") are provided which are structurally similar to organophosphate pesticides but which, in contrast to organophosphate pesticides, may be conjugated to antigenic macromolecules.

The invention therefore provides immunoconjugates for use in preparing antibodies or fragments thereof which are capable of binding to "parent" organophosphate compounds and also the antibodies (or fragments) thus prepared. Such antibodies can be polyclonal or monoclonal with monoclonal antibodies being preferred.

A method for detecting the presence of an organophosphate in a sample, and assay kits therefor are also provided, the method comprising the step of assaying the sample with an antibody or fragment thereof as provided by the invention. For such methods, the antibody can optionally be labelled or bound to a support or both.

The methods of the invention are applicable to all classes of organophosphates. This ability to raise antibodies to all organophosphates using the generic haptens of the invention represents a very great advance over the known art in this field, the implications of which will be well understood by those persons skilled in the art.

It will also be appreciated by those persons skilled in the art that the above description is provided by way of example only and that numerous variations and modifications maybe made without departing from the scope of the present invention.

We claim:

1. A compound useful for forming immunoconjugates used in the detection of organophosphate pesticides, said compound having the formula

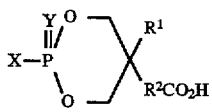

wherein X is selected from the group consisting of R—O—, R—S— and R—NH—, where R is an optionally substituted aromatic or heterocyclic group, or an optionally substituted alkyl or alkenyl group;

Y is O or S;

$R^1$ is H or alkyl; and $R^2$ is a group of the formula —$(CH_2)_n$— wherein n is an integer of from 1 to 10, or branched chain alkylene, or a group of the formula $R^3$—O—$R^4$ wherein $R^3$ and $R^4$ are both or straight or branched chain alkylene;

or a salt or ester thereof.

2. A compound of the formula:

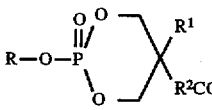 (IA)

wherein R, $R^1$ and $R^2$ are as defined in claim 1.

3. A compound of the formula:

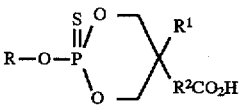 (IB)

wherein R, $R^1$ and $R^2$ are as defined in claim 1.

4. A compound of the formula:

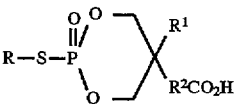 (IC)

wherein R, $R^1$ and $R^2$ are as defined in claim 1.

5. A compound of the formula:

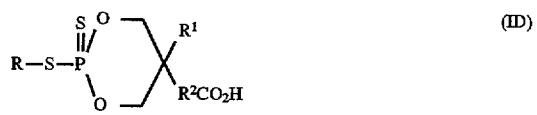 (ID)

wherein R, $R^1$ and $R^2$ are as defined in claim 1.

6. A compound of the formula:

 (IE)

wherein R, $R^1$ and $R^2$ are as defined in claim 1.

7. A compound of the formula:

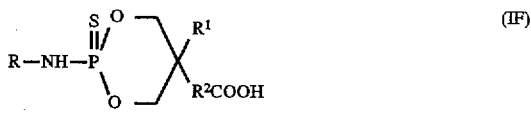 (IF)

wherein R, $R^1$ and $R^2$ are as defined in claim 1.

8. A compound as claimed in claim 1 wherein $R^2$ is a group of the formula $R^3$—O—$R^4$ wherein $R^3$ and $R^4$ are both —$CH_2$—.

9. A compound as claimed in claim 1 wherein $R^1$ is H or $C_{1-6}$ alkyl and $R^2$ is a group of the formula —$(CH_2)_n$— wherein n is an integer from 1 to 6.

10. A compound as claimed in claim 1 of the formula

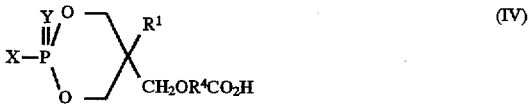 (IV)

wherein X and Y are as defined in claim 1;

$R^1$ is —H, —$CH_3$, or —$CH_2CH_3$; and $R^4$ is as defined in claim 1;

or a salt or ester thereof.

11. A compound as claimed in claim 10 wherein $R^4$ is —$CH_2$—.

12. A compound as claimed in claim 1 wherein $R^1$ is —H or —$CH_3$ and $R^4$ is —$CH_2$—.

13. A compound as claimed in claim 1 wherein said compound is 2-[5-methyl-2-(3,5,6-trichloropyridin-2-oxy)-1,3,2-dioxaphosphorinan-5-yl,2-sulfide]methoxyacetic acid, or a salt or ester thereof.

14. A compound as claimed in claim 1 wherein said compound is 2-[5-methyl-2-(4-nitrophenoxy)-1,3,2-dioxaphosphorinan-5-yl, 2-sulfide]methoxyacetic acid, or a salt or ester thereof.

15. A compound as claimed in claim 1 wherein said compound is 2-[5-methyl-2-(4-nitrophenoxy)-1,3,2-dioxaphosphorinan-5-yl,2-oxide]methoxyacetic acid, or a salt or ester thereof.

16. A compound as claimed in claim 1 wherein said compound is 2-[[5-methyl-2-[(4-oxo-1,2,3-benzotriazin-3 (4H)-yl)methyl-thio]-1,3,2-dioxaphosphorinan-5-yl,2-sulfide]]methoxyacetic acid, or a salt or ester thereof.

17. A compound as claimed in claim 1 wherein said compound is 2-[[-5-methyl-2-[2-(methylamino)-2-oxoethylthio]-1,3,2-dioxaphosphorinan-5-yl,2-sulfide]] methoxyacetic acid, or a salt or ester thereof.

18. A compound as claimed in claim 1 wherein said compound is 2-[2-(2,2-dichloroethenyloxy)-5-methyl-1,3,2-dioxaphosphorinan-5-yl, 2-oxide]methoxyacetic acid, or a salt or ester thereof.

19. A compound as claimed in claim 1 wherein said compound is 2-[[2-[2-(ethylthio)-ethylthio]-5-methyl-1,3,2-dioxaphosphorinan-5-yl,2-oxide]]methoxyacetic acid, or a salt or ester thereof.

20. A compound as claimed in claim 1 wherein said compound is 5[2-(4-nitrophenoxy)-1,3,2-dioxaphosphorinanyl,2-sulfide]pentanoic acid, or a salt or ester thereof.

21. An immunoconjugate comprising a compound as claimed in claim 1 conjugated to an antigenic macromolecule.

22. An immunoconjugate as claimed in claim 21 wherein said macromolecule is a protein.

23. An immunoconjugate as claimed in claim 22 wherein the protein is ovalbumen, bovine serum albumen, mouse albumen or polylysine.

24. A method of producing an antibody or binding fragment thereof comprising the step of immunising an animal with an immunoconjugate as claimed in claim 21.

25. A method as claimed in claim 24 which includes the further step of recovering said antibody or fragment resulting from the immunisation step.

26. A method of producing a hybridoma cell line which comprises the step of immortalising an antibody-producing cell obtained from an animal immunised with an immunoconjugate as claimed in claim 21.

27. A method for producing an antibody or binding fragment comprising the step of expressing DNA coding therefor in a recombinant host cell, said DNA having been obtained from an antibody-producing cell of an animal immunised with an immunoconjugate as claimed in claim 21.

28. A method as claimed in claim 27 wherein said antibody-producing cell is a spleen cell.

29. A compound for use in preparing a compound of the formula I defined in claim 1, wherein said compound is selected from the group of compounds of the formulae:

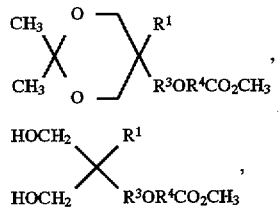

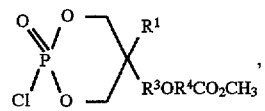

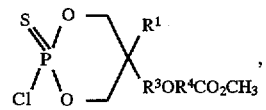

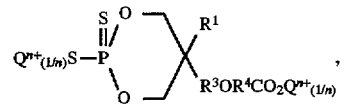

and

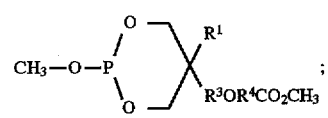

wherein, in the above formulae, $R^1$ is H or alkyl, $R^3$ and $R^4$ are both straight or branched chain alkylene and $Q^{n+}$ is a cation having a positive charge n.

30. A compound as claimed in claim 29, said compound being selected from the group consisting of:

2(2,2,5-trimethyl-1,3-dioxan-5-yl)methoxyacetic acid, methyl ester,

2(3-hydroxy-2-hydroxymethyl-2-methyl)propoxyacetic acid, methyl ester,

2(2-chloro-5-methyl-1,3,2-dioxaphosphorinan-5-yl,2-sulfide)methoxyacetic acid, methyl ester, 2(2-chloro-5-methyl-1,3,2-dioxaphosphorinan-5-yl,2-oxide)methoxyacetic acid, methyl ester, 2-(2-mercapto-5-methyl-1,3,2-dioxaphosphorinan-5-yl,2-sulfide)methoxyacetic acid, bispotassium salt, and (2-methoxy-5-methyl-1,3,2-dioxaphosphorinan-5-yl)methoxyacetic acid, methyl ester.

* * * * *